US011060926B2

(12) United States Patent
Reif et al.

(10) Patent No.: US 11,060,926 B2
(45) Date of Patent: Jul. 13, 2021

(54) SENSOR ASSEMBLIES; SENSOR-ENABLED GARMENTS AND OBJECTS; DEVICES AND SYSTEMS FOR DATA COLLECTION

(71) Applicant: Sensoria, Inc., Redmond, WA (US)

(72) Inventors: Roberto Reif, Seattle, WA (US); Maria Pia Carmagnani, Redmond, WA (US); Warren Kline, Ottawa (CA); Dave Svab, Woodinville, WA (US); Maurizio Macagno, Redmond, WA (US); Chris Small, Seattle, WA (US); Blake Coudriet, Puyallup, WA (US); Matthew Kueper, Indianola, WA (US)

(*) Notice: Subject to any disclaimer, the term of this patent is extended or adjusted under 35 U.S.C. 154(b) by 0 days.

(21) Appl. No.: 16/095,268

(22) PCT Filed: Apr. 21, 2017

(86) PCT No.: PCT/US2017/028976
§ 371 (c)(1),
(2) Date: Oct. 19, 2018

(87) PCT Pub. No.: WO2017/185050
PCT Pub. Date: Oct. 26, 2017

(65) Prior Publication Data
US 2019/0094088 A1 Mar. 28, 2019

Related U.S. Application Data

(60) Continuation-in-part of application No. 14/908,502, filed as application No. PCT/US2014/049263 on Jul.
(Continued)

(51) Int. Cl.
*G01L 1/00* (2006.01)
*G01L 1/18* (2006.01)
(Continued)

(52) U.S. Cl.
CPC .............. *G01L 1/18* (2013.01); *A43B 3/0005* (2013.01); *A43B 17/00* (2013.01); *A61B 5/1038* (2013.01);
(Continued)

(58) Field of Classification Search
CPC ........... G01L 1/18; G01L 1/205; G16H 50/20; G16H 40/63; G16H 20/30; G16H 50/30;
(Continued)

(56) References Cited

U.S. PATENT DOCUMENTS 5,678,448 A * 10/1997 Fullen ................. A61B 5/1036
600/592
6,195,921 B1 * 3/2001 Truong .................... A43B 3/00
340/573.1
(Continued)

*Primary Examiner* — Max H Noori

(57) ABSTRACT

Components and assemblies for acquisition and analysis of data collected from sites such body surfaces, footwear and apparel, objects, accessories, and the like are directed to providing intermittent and/or continuous monitoring and reporting of conditions such as force, pressure, shear and other conditions, activity and/or environmental parameters at body locations and/or at an interface of a body location and an object. In one aspect, sensor assemblies comprise one or more sensor(s) and/or associated electronics associated with at least one non-conductive carrier layer. Electronic components including sensor acquisition systems (SAS) and dedicated electronics devices (DED) providing electronics components for signal conditioning, data collection, storage, analysis, feedback, communications and optional sensing capabilities are also described.

15 Claims, 16 Drawing Sheets

Related U.S. Application Data 31, 2014, now abandoned, said application No. PCT/US2017/028976 is a continuation-in-part of application No. 14/574,220, filed on Dec. 17, 2014, now abandoned, which is a division of application No. 13/753,456, filed on Jan. 29, 2013, now Pat. No. 8,925,392, said application No. PCT/US2017/028976 is a continuation-in-part of application No. 15/311,471, filed as application No. PCT/US2015/030899 on May 14, 2015, now abandoned, and a continuation-in-part of application No. 14/908,502, filed as application No. PCT/US2014/049263, application No. 16/095,268, which is a continuation-in-part of application No. 16/067,999, filed as application No. PCT/US2016/068499 on Dec. 23, 2016, now abandoned, application No. 16/095,268, which is a continuation-in-part of application No. 15/540,404, filed as application No. PCT/US2015/068180 on Dec. 30, 2015, now abandoned.

(60) Provisional application No. 62/325,901, filed on Apr. 21, 2016, provisional application No. 62/458,795, filed on Feb. 14, 2017, provisional application No. 61/860,869, filed on Jul. 31, 2013, provisional application No. 61/592,333, filed on Jan. 30, 2012, provisional application No. 61/747,877, filed on Dec. 31, 2012, provisional application No. 61/994,054, filed on May 15, 2014, provisional application No. 62/274,707, filed on Jan. 4, 2016, provisional application No. 62/163,861, filed on May 19, 2015, provisional application No. 62/099,099, filed on Dec. 31, 2014.

(51) Int. Cl.
| | |
|---|---|
| *A61B 5/11* | (2006.01) |
| *A43B 17/00* | (2006.01) |
| *A61B 5/00* | (2006.01) |
| *A61B 5/103* | (2006.01) |
| *A43B 3/00* | (2006.01) |
| *G01L 1/20* | (2006.01) |
| *G16H 40/63* | (2018.01) |
| *G16H 50/20* | (2018.01) |
| *A43D 1/02* | (2006.01) |
| *G16H 50/30* | (2018.01) |
| *A61B 5/024* | (2006.01) |
| *A61B 5/01* | (2006.01) |
| *G16H 20/30* | (2018.01) |

(52) U.S. Cl.
CPC .............. *A61B 5/11* (2013.01); *A61B 5/6802* (2013.01); *A61B 5/6807* (2013.01); *G01L 1/205* (2013.01); *G16H 40/63* (2018.01); *G16H 50/20* (2018.01); *A43D 1/027* (2013.01); *A61B 5/002* (2013.01); *A61B 5/01* (2013.01); *A61B 5/024* (2013.01); *A61B 5/1036* (2013.01); *A61B 5/447* (2013.01); *A61B 5/6831* (2013.01); *A61B 2560/0223* (2013.01); *A61B 2560/045* (2013.01); *A61B 2562/0247* (2013.01); *A61B 2562/16* (2013.01); *A61B 2562/227* (2013.01); *D10B 2401/18* (2013.01); *G16H 20/30* (2018.01); *G16H 50/30* (2018.01)

(58) Field of Classification Search
CPC ..... A43B 3/0005; A43B 17/00; A61B 5/1038; A61B 5/11; A61B 5/6802; A61B 5/6807; A61B 5/002; A61B 5/01; A61B 5/1036; A61B 5/447; A61B 5/6831; A61B 2560/0223; A61B 2560/045; A61B 2562/0247; A61B 2562/16; A61B 2562/227; A43D 1/027; D10B 2401/18
USPC ..................................................... 73/862.541
See application file for complete search history.

(56) References Cited

U.S. PATENT DOCUMENTS

| | | | |
|---|---|---|---|
| 2013/0192071 A1* | 8/2013 | Esposito | A61B 5/1036 33/6 |
| 2016/0367191 A1* | 12/2016 | Esposito | A61B 5/1038 |
| 2017/0086519 A1* | 3/2017 | Vigano' | A61B 5/225 |
| 2019/0159727 A1* | 5/2019 | Macagno | A43B 3/0005 |

* cited by examiner

SENSOR ASSEMBLIES; SENSOR-ENABLED GARMENTS AND OBJECTS; DEVICES AND SYSTEMS FOR DATA COLLECTION

REFERENCE TO RELATED APPLICATIONS

This application is the US national phase entry of International Patent Application No. PCT/US2017/028976, filed Apr. 21, 2017, which claims the benefit of U.S. Patent Application Nos. 62/325,901, filed Apr. 21, 2016 and 62/458,795, filed Feb. 14, 2017. This application is a continuation-in-part of pending U.S. patent application Ser. No. 14/908,502, filed Jan. 28, 2016, which is a US national phase entry of International Patent Application No. PCT/US2014/049263, filed Jul. 31, 2014, which claims the benefit of U.S. Provisional Patent Application No. 61/860,869, filed Jul. 31, 2013, and which is a continuation-in-part application of U.S. patent application Ser. No. 14/574,220, filed Dec. 17, 2014, which is a divisional application of U.S. patent application Ser. No. 13/753,456, filed Jan. 29, 2013, which claims the benefit of U.S. Patent Application Nos. 61/592,333 filed Jan. 30, 2012 and 61/747,877 filed Dec. 31, 2012. This application is a continuation-in-part of pending U.S. patent application Ser. No. 15/311,471, filed Nov. 15, 2016, which is a US national phase entry of International Patent Application No. PCT/US2015/030899, filed May 14 2015, which claims the benefit of U.S. Provisional Patent Application No. 61/994,054, filed May 15, 2014 and which is a continuation-in-part application of U.S. patent application Ser. No. 14/574,220, filed Dec. 17, 2014, which is a divisional application of U.S. patent application Ser. No. 13/753,456, filed Jan. 29, 2013, which claims the benefit of U.S. Patent Application Nos. 61/592,333 filed Jan. 30, 2012 and 61/747,877 filed Dec. 31, 2012. This application is a continuation-in-part of pending U.S. patent application Ser. No. 16/067,999, filed Jul. 3, 2018, which is a US national phase entry of International Patent Application No. PCT/US2016/068499, filed Dec. 23, 2016, which claims the benefit of U.S. Provisional Patent Application No. 62/274,707, filed Jan. 4, 2016 and is a continuation-in-part of pending U.S. patent application Ser. No. 15/540,404, filed Jun. 28, 2017, which is a US national phase entry of International Patent Application No. PCT/US2015/068180, filed Dec. 30, 2015, which claims the benefit of US Provisional Patent Application Nos. 62/099,099, filed Dec. 31, 2014 and 62/163,861, filed May 19, 2015. The priority patent applications are incorporated herein by reference in their entireties.

FIELD

The present disclosure relates generally to sensor assemblies, including sensor assemblies associated with or incorporated in garments intended to contact a body surface (directly or indirectly), to sensor assemblies incorporated in or applied to objects, to sensor interfaces with electronic components and devices, and to associated electronic devices. Several aspects of sensor assembly components, data collection systems and integration of sensor assemblies with garments and objects are disclosed.

BACKGROUND

Various types of sensing systems have been incorporated in shoes, insoles, socks and other types of garments for monitoring a variety of physiological and environmental parameters for various applications, including recreational, fitness, sporting, military, diagnostic and medical applications. The use of sensing systems for fitness applications to monitor and analyze activities such as running, walking, energy expenditure, location and the like, is now common. Medical applications for sensing pressure, temperature and the like for purposes of monitoring neuropathic and other degenerative conditions with the goal of alerting an individual and/or medical service providers to sensed parameters that may indicate the worsening of a condition, lack of healing, and the like, have been proposed. Footwear-related sensing systems directed to providing sensory data for patients suffering from neuropathy, for gait analysis, rehabilitation assessment, shoe research, design and fitting, orthotic design and fitting, and the like, have been proposed.

Sensing devices and footwear having sensors incorporated for monitoring pressure and other body parameters have been proposed. Various types of sensing systems for monitoring various physiological parameters have been incorporated in bands, wrist-worn devices, portable electronic devices, medical devices, shoes, insoles, socks and other types of garments for various applications. The use of sensing systems for fitness applications to monitor and analyze activities such as running, walking, energy expenditure, and the like, is now common.

Many of the existing systems are designed to meet specific requirements of the sensor data to be captured. Changes in sensor type and characteristic may require re-design of a significant part of the system, even when limited changes are required. As sensing devices and systems are incorporated into a wide array of garments, footwear, objects and accessories, the number of different designs and form factors, and the capability of capturing disparate data becomes challenging. Providing a modular sensing and data collection system adapted for use in different environments and for capturing and using different types of information collected from different data collection points and different types of sensors would be highly advantageous.

SUMMARY

In one aspect, components and assemblies for acquisition and analysis of data collected from sites such body surfaces, footwear and apparel, objects (e.g., sporting objects, tools, etc.), accessories, and the like described herein are directed to providing intermittent and/or continuous monitoring and reporting of conditions such as force, pressure, shear and other conditions, activity and/or environmental parameters at body locations and/or at an interface of a body location and an object, and analyzing and reporting activity parameters and providing feedback to the user or a third party. Sensor assemblies, interfaces, systems and materials described herein are used for acquisition, collection and analysis of physiological, biomechanical and/or environmental data from body sites such as feet and other body parts, objects, accessories, etc., may be used for a variety of sports-related, military, fitness, medical, diagnostic and therapeutic purposes.

In one aspect, sensor assemblies disclosed herein comprise one or more sensor(s) and/or associated electronics contacting or mounted or bonded or adhered to or incorporated or integrated in (referred to herein, collectively, as "associated with") at least one substantially non-conductive carrier layer. The carrier layer(s) provides a convenient and versatile assembly substrate and substantially insulates the sensor(s), conductive traces and associated electronic components from undesired interference resulting in signal degradation. "Substantially non-conductive" means, in this context, that the carrier layer(s) is not appreciably electrically conductive and does not interfere with or alter electrical or electronic signals conveyed to or from the sensor(s) along conductive trace pathways. In some embodiments, the carrier layer(s) is substantially impermeable to liquids. "Substantially impermeable" means, in this context, that the carrier layer(s) inhibits or prevents penetration of liquids through the carrier layer(s) sufficient to inhibit or prevent degradation or alteration of sensing or electrical signals resulting from moisture. The carrier layer(s) may also prolong the life expectancy of the sensor(s), conductive traces and associated electronic components, protecting these components from friction and exposure to potentially damaging agents such as light, heat, detergents, water, moisture and the like.

In some embodiments, sensor assemblies are associated with and positioned between two substantially non-conductive carrier layers to provide an encapsulated sensor assembly. In some embodiments, sensor(s), optional leads or conductive traces may be mounted on a substrate for assembly purposes, and the substrate with associated sensors, leads and/or traces may be associated with and positioned between two substantially non-conductive carrier layers. "Encapsulated," in this context, means that the sensor(s) and conductive trace(s) are sandwiched between and contact opposing substantially non-conductive carrier layers. The opposing carrier layers contact, but may or may not be bonded or adhered to one another in areas where they contact to provide a sealed, encapsulated assembly. One or more encapsulated sensor assemblies may be associated with a substrate such as a garment, footwear, sports-related object, diagnostic or therapeutic object, occupational object, or the like to provide an instrumented, sensor-enabled item.

Discrete sensor assemblies having any desired arrangement of sensor(s) and associated electronic components and being associated with at least one non-conductive carrier layer may be mounted to or incorporated or integrated in, or bonded or adhered to (collectively, "associated with") a substrate such as footwear, a garment, or any of a variety of objects or accessories, and coupled to sensor interface terminals (e.g., signal transfer and signal receipt terminals and optional common terminal(s)) to provide sensor-enabled footwear, garments, objects and accessories. Footwear and garments incorporating such sensor systems may be comfortably worn by users and contact a body surface of users under many conditions to provide real time monitoring of conditions at or near body surfaces.

Sensor assemblies having different types and arrangements of sensors, (optional) leads, traces and signal transfer terminals may be quickly and conveniently designed and produced for use in different sensing applications, garments, objects, and the like, providing versatile and adaptive sensor assemblies. In some embodiments, kits for assembling sensor assemblies comprising discrete sensor assembly components may be provided to users for use in assembling sensor assemblies to their specifications. Such kits for assembling sensor assemblies may comprise, for example, one or more sensor(s), optional leads, conductive traces or materials for making conductive traces, signal terminals or materials for making signal terminals, carrier templates or materials for making carrier templates, electronic components such as signal acquisition systems and dedicated electronic devices, and instructions for assembling sensor assemblies comprising these components.

In some embodiments, sensors are capable of sensing a physiological parameter of the underlying skin or tissue. In some embodiments, sensors are capable of and configured for sensing force and/or pressure and/or shear exerted on or against an underlying skin or tissue, or an underlying surface. In some aspects, sensors are capable of sensing temperature, conductive impulses, or other properties associated with a body surface, tissue or object. In some embodiments, sensors may operate using a variety of mechanisms and may produce signals resulting, for example, from resistive and/or conductive and/or capacitive and/or inductive properties and changes in those properties. Sensors may additionally or alternatively provide data relating to stretch, light, temperature, moisture, humidity, stress, strain, electromyography, electroencephalography, heart rate, respiratory rate, blood pressure, blood oxygen saturation, blood flow, breathing rate, local gas content, galvanic skin response, bacterial content, and the like. One or more additional sensors may be capable of and configured for sensing environmental conditions such as location, position in space, orientation, acceleration, multi-axis acceleration, multi-axis gyroscope, multi-access magnetometer, and the like. A variety of such sensors are known in the art and may be adapted for use in sensing systems described herein.

In some embodiments implementing sensors for detecting and monitoring force and/or pressure and/or shear exerted on or against an underlying skin or tissue or an underlying surface, the sensor(s) may comprise pliable, electrically resistive and/or conductive fabric materials, fibers, yarns, and the like. In some embodiments, sensors comprise other types of flexible conductive or resistive materials, such as conductive or resistive thermoplastic elastomers (TPEs), conductive or resistive inks, conductive or resistive silicone-containing materials, or similar flexible materials capable of manifesting a dielectric behavior. In some embodiments, conductive traces may comprise pliable, electrically conductive fabric materials, threads, yarns, or the like. In some embodiments, conductive traces may comprise conductive inks or conductive elastomers or conductive silicone-containing materials associated with (e.g., applied to) the carrier layer.

In me embodiments, one or more resistive sensor(s) detects changes in voltage or resistance across a surface area that is associated with force exerted on the sensor, which is related to pressure (as force per unit surface area) and/or shear. Force, pressure, shear and measurements or values that are derivative thereof may therefore be determined at identifiable spatial locations where sensors are positioned. In some embodiments, resistive sensors capable of providing proportional pressure signals (e.g., proportional pressure sensed over a surface area), and/or providing pressure signals that correlate with spatial locations on a surface area of the resistive sensors are used.

In some embodiments, FSR (Force Sensitive Resistor) or piezo-resistive sensors may be used. One type of piezoresistive force sensor that has been used previously in footwear pressure sensing applications, known as the FLEXIFORCE® sensor, can be made in a variety of shapes and sizes and measures resistance, which is inversely proportional to applied force. These sensors use pressure sensitive inks with silver leads terminating in pins, with the pressure sensitive area and leads sandwiched between polyester film layers. FLEXIFORCE® sensors are available from Tekscan, Inc., 307 West First Street, South Boston, Mass. 02127-1309 USA. Other types of sensors, including sensors employing conductive electrodes, may also be associated with various substrate materials (e.g., garments, sheet materials and the like).

In some embodiments, sensors and/or associated leads and/or conductive traces incorporated in sensing systems as described herein comprise materials such as flexible, resistive and/or conductive "e-textile" fabric and/or yarn material(s), fibers or the like. In some embodiments, sensors and/or associated leads and/or conductive traces incorporated in sensing systems comprise flexible, resistive and/or conductive fabric or yarn materials that are substantially isotropic with respect to their flexibility and/or stretch properties. By "substantially" isotropic, we mean to include materials that have no more than a 15% variation and, in some embodiments, no more than a 10% variation in flexibility and/or stretch properties in any direction, or along any axis of the material. Suitable materials, such as resistive and/or piezoresistive or conductive fabric and yarns, coated and/or impregnated fabrics and yarns, such as metallic coated fabric and yarn materials and fabric and yarn materials coated or impregnated with other types of resistive or conductive formulations, are known in the art and a variety of such fabric and yarn materials may be used. In some embodiments, pressure sensors comprise flexible resistive woven fabric material that is stretchable and/or elastic and/or substantially isotropic with respect to its flexibility and/or stretch properties.

Fabrics and yarns comprising a knitted nylon/spandex substrate coated with a resistive formulation are suitable for use, for example, in fabricating biometric e-textile pressure sensors and in other applications requiring environmental stability and conformability to irregular configurations. One advantage of using these types of e-textile sensors is that they perform reliably in a wide variety of environments under different temperature and moisture conditions), and they're generally flexible, durable, washable, and comfortably worn against the skin. Suitable flexible resistive fabric and yarn materials are available, for example, from VTT/Shieldex Trading USA, 4502 Rt-31, Palmyra, N.Y. 14522, from Statex Productions & Vertriehs GmbH, Kleiner Ort 11 28357 Bremen Germany, and from Eeonyx Corp., 750 Belmont Way, Pinole, Calif. 94564.

Techniques for deriving force and/or pressure and/or shear measurements using e-textile materials are known in the art and various techniques may be suitable. See, e.g., http://www.kobakantat/DIY/?p=913. Techniques for measuring other parameters using e-textile materials, such as humidity and temperature measurements, are also known and may be used in sensing systems herein. See, http://www.nano-tera.ch/pdf/posters2012/TWIGS105.pdf. E-textile sensors may thus be capable of monitoring various parameters, including force, pressure, shear, humidity, temperature, gas content, and the like, at the sensor site. Additional monitoring capabilities may be available using e-textile sensors as innovation in fabric sensors proceeds and as nano-materials and materials incorporating nano-structures are developed and become commercially feasible. Additional detection and monitoring capabilities may be provided using different types of sensors as well. Different types of sensors using different sensing technologies may be combined and associated with a carrier in sensor assemblies as described herein.

Sensor assemblies and systems described herein thus comprise at least one flexible sensor (or means for sensing) and one or more flexible conductive traces (or conductive pathway means) associated with a non-electrically conductive flexible carrier (means) that can be associated with footwear, a garment, an object, or an accessory by bonding, integration, adhering affixing, or the like. In some embodiments, sensor assemblies may additionally comprise at least one signal transfer terminal and/or at least one common terminal operatively coupled to at least one trace and associated with the non-electrically conductive, flexible carrier. Each sensor may be connected to a common or ground trace that terminates at a common terminal during operation to provide grounding, power or other communication pathways to and from sensor.

In some embodiments, the sensor assemblies described herein are connected or connectible to ("operably coupled to") electronics components providing signal conditioning, data collection, analysis, feedback, and the like. In some embodiments, at least one sensor acquisition system (SAS) comprises electronic components associated with a sensor assembly incorporated in footwear, garments, objects or accessories. In some embodiments, the SAS may simply provide signal pathways and electrical contacts between terminals of the sensor assembly associated with the footwear, garment or object and an external electronics device. In some embodiments, the SAS may provide signal pathways and electrical contacts, and may also have electronics configured to condition signals, such as to filter and/or amplify and/or modify raw data signals acquired from a sensor, and/or to reduce signal noise. In some embodiments, the SAS may additionally house one or more sensors and/or components providing data relating to, for example, time, temperature, moisture, location, altitude, position, orientation, movement, acceleration, and the like. In some embodiments, the SAS may house haptic feedback components to actively alert the wearer about some specific event. In some embodiments, the SAS may house at least one of an accelerometer, a multi-axis accelerometer, a gyroscope, a multi-axis gyroscope, a magnetometer, and a multi-axis magnetometer.

The SAS may have one or more data acquisition channels corresponding to sensor(s) located in associated sensor assemblies and/or sensor(s) located in the SAS itself. Different SAS configurations may provide different data acquisition channels and may have different electronic designs and capabilities for treating data signals of different types, acquired from different types of sensors. Signals received and optionally conditioned by the SAS may depend on the sensor type used. In some embodiments, the SAS is configured to acquire and condition signals relating to resistive and/or conductive and/or capacitive and/or inductive properties of a sensor. Changes in sensing stimulus for these types of sensors may be detected as changes in the voltage, current, resistance, conductance, capacitance and/or inductance of the sensor. In many embodiments, the signals generated at the sensor(s) in response to sensed stimulus and received by the SAS are proportional to the sensing stimulus. In some embodiments, the SAS may be provided as a generic component that can be customized to coordinate with different types of sensors and sensor assemblies, as appropriate, by incorporating different electronic values.

SAS components may be provided separately from or housed in combination with a dedicated electronic device (DED) providing data collection, analysis, or the like. In some embodiments, for example, an SAS component may be permanently or detachably associated with footwear, a garment or an object with which the sensor assembly is associated and may be configured as a docking component having a predetermined conformation for detachably receiving a mating DED component. Discrete SAS and DED components that can be operably coupled to and also detached from one another have complementary mechanical and electrical configurations for facilitating convenient and high fidelity mating of the components and operable communication of electrical signals and data between the components. In some embodiments, mechanical connection of SAS and DED terminals provided in separate components may be facilitated by complementary, mating three-dimensional features, reference marks or other types of visual and/or mechanical alignment mechanisms provided on the separate components that indicate proper interface orientations.

In some embodiments, a DED component may be operatively coupled to a discrete (separate) SAS component via conductive traces provided on a printed circuit board (PCB), or via conductive connections such as pogo pins and/or magnetic or other types of contacting connections. In some embodiments, the mating terminals may comprise conductive pins, including stationary conductive pins as well as movable pins, such as spring-loaded pins, referred to as pogo pin connectors. In some embodiments, easy and secure mating of the terminals may be enhanced using magnetic mechanisms or other types of mechanisms that help users to properly and securely align and connect/disconnect the mating terminals with minimal effort. In some embodiments, easy and secure mating of the terminals may be enhanced by complementary (and/or locking) mechanical configurations of housing components associated with mating terminals. In some embodiments, mating terminals provided on the SAS and on a DED are provided in a predetermined arrangement, or have a keyed configuration, to ensure that the DED is properly aligned and mounted to the terminals provided on the substrate in a predictable and pre-determined orientation.

The SAS generally comprises a lightweight and water-tight enclosure for the data collection terminals, optional sensors, signal conditioning and processing electronics. In some embodiments, the SAS can be customized for a specific applications and specific sensor assemblies. Customized SAS components may be provided, for example, for different sensor types and sensor assemblies used in different types of footwear (e.g., running shoes, ski boots, insoles, soccer shoes, and the like), garments (e.g., shirts, shorts, pants, bands, and the like), objects (such as golf-clubs, racquets, bats, gloves, tools and occupational objects, cushions, upholstery, steering wheels, and the like.

In some embodiments, the SAS may be configured to store information that may be communicated to a mating DED and transfer data relating to the specifics of the SAS and the sensing assembly associated with the SAS to the DED upon mating of the DED with the SAS. In some embodiments, for example, data such as discrete item serial numbers, footwear, garment or object type and size, location of SAS on the footwear, garment or object, (such as left, right, top, bottom), number, type and configuration of sensors, signal and data type and value range, calibration data, user data, and the like may be stored in an SAS associated with the object and communicated to a mating DED. The information may be included in an integrated memory or other electronic component associated with the SAS, such as an EEPROM and/or via jumpers or other electronically hardcoded means. The DED, once mated to a specific SAS having such stored information, may use such information to provide appropriate signal processing and analysis, determine the system behavior and enable specific algorithms or firmware/software routines and modules to properly process the incoming sensor signals. In some embodiments, this type of information—e.g., discrete item serial numbers, footwear, garment or object type and size, location of SAS on the footwear, garment or object, (such as left, right, top, bottom), number, type and configuration of sensors, signal and data type and value range, calibration data, user data, and the like—may be stored in a DED associated with the object and communicated to a mating SAS.

The DED electrically and operably connects to the signal transfer and/or common terminal(s) of the sensor assembly and/or SAS and serves as (temporary or permanent) data collection and/or analysis device. The DED generally comprises a lightweight and water-tight enclosure for the data collection and processing electronics and (optional) energy source and provides signal receiving terminals that mate with the signal transfer terminals of an SAS or a sensor assembly. In some embodiments, the DED is provided as a bendable or partially bendable device that can be shaped, as desired, to closely contact a sensor assembly or an SAS receptacle.

The DED, in addition to having data recording, processing and/or analysis capabilities, may incorporate an energy source such as a battery providing energy for data recording, processing and/or analysis, as well as providing energy for operation of one or more of the sensor(s). The energy source may comprise a rechargeable and/or replaceable battery source, and/or a regenerative energy system. In some embodiments, the DED or other external devices may be configured to program sensor(s), SAS devices, and the like, using the conductive traces as interface pathways. The DED may additionally be configured to communicate with one or more external electronic device(s), such as a smartphone, personal computing device/display, host computer, base station (or hub) or the like for signal transfer, processing, analysis and display to a user and/or others. In some embodiments, the DED may also be configured to communicate with other DEDs located in proximity, such as via a dynamic "mesh network," to facilitate the communication and transport of data to external electronic devices(s) such as a smartphone, personal computing device/display, host computer, base station (or hub). A mesh network has a topology whereby all devices can communicate with all other devices in the network, either directly if in range, indirectly via one or more intermediate "nodes" if they are not. This is in contrast to other network types that often feature a central hub like a router, through which all traffic must flow. Mesh networks have no such central hub and offer multiple ways of getting data from one device to another.

In some embodiments, the SAS and/or the DED may be configured to communicate with an external, hosted computing system (operated, e.g., at a centralized, hosted facility and/or "Cloud") that provides additional data analysis, formulates feedback, notifications, alerts, and the like, that may be displayed to the user, a coach, a caretaker, a clinician, or the like, through one or more computing and/or display devices. In alternative embodiments, the DED may itself perform signal processing and analysis, and may display or otherwise communicate feedback directly to a user without interfacing with an external computing device. Substantially real-lime feedback, including data displays, notifications, alerts and the like, may be provided to the user, caretaker and/or clinician according to user, caretaker and/or clinician preferences.

In operation, an authentication routine and/or user identification system matches the DED and an associated SAS and sensor assembly with a user, a community of users, a caretaker and/or clinician, and may link user information and data from other sources to a software- and/or firmware-implemented system residing on the external computing system. The external computing device may itself communicate with a centralized host computing system or facility where data is stored, processed, analyzed, and the like, and where output, communications, instructions, commands, and the like may be formulated for delivery back to the user, caretaker and/or clinician through the external computing device and/or the DED.

Calibration routines may be provided to ensure that the SAS and/or the DED and any connected sensor system are properly configured to work optimally for the specific user, sensor assembly and application. Configuration and setup routines may be provided to guide the user (or caretaker or medical professional) to input user information and data to facilitate data collection, and various protocols, routines, data analysis and/or display characteristics, and the like, may be selected by the user (or caretaker or medical professional) to provide data collection and analysis that is targeted to specific users. Specific examples are provided below. Notification and alarm systems may be provided, and selectively enabled, to provide messages, warnings, alarms, and the like to the user, and/or to caretakers and/or medical providers, substantially in real-time, based on sensed data.

Various other aspects of sensing systems and background relating to the construction, use and utility for such sensing systems are described in the following previously published and commonly owned patent publications, all of which are incorporated herein by reference in their entireties: U.S. Pat. Nos. 8,925,392 and 9,186,092; PCT Patent Publication WO 2013/116242 A2; PCT Patent Publication WO 2015/017712 A1; PCT Patent Publication WO 2015/175838 A1; PCT Patent Publication WO 2015/103442; PCT Publication WO 2016/109744; and U.S. Patent Publication US 2016/0367191.

BRIEF DESCRIPTION OF THE DRAWINGS

FIG. 1A shows a side view illustrating encapsulated conductive traces bonded to the sock and SAS/DED combination mounted in an ankle area of the sock; FIG. 1B shows a perspective view of the instrumented sock illustrating a plurality of encapsulated sensors positioned and bonded to a plantar area of the sock, associated encapsulated traces and an SAS/DED combination mounted in an ankle area of the sock.

FIG. 2A shows an exemplary substrate interface carrier (for contacting an underlying substrate such as footwear, a garment, an object, or the like), and FIG. 2B illustrates an electronics interface carrier template complementary to the substrate interface carrier template and configured for association with an SAS and/or DED having complementary terminal types and locations.

FIG. 5A shows an embodiment in which sensors are operatively coupled to a discrete SAS component, and the discrete SAS component is operatively coupled to a discrete DED component. FIG. 5B shows an embodiment in which sensors are operatively coupled to an electronics component providing both SAS and DED functions.

FIG. 6A shows one top perspective view of the device illustrating the contours of the docking receptacle and showing an alignment recess in one internal receptacle wall; FIG. 6B shows another top perspective view of the device of FIG. 6A rotated 90° from the perspective shown in FIG. 6A; FIG. 6C shows a bottom view of the device of FIG. 6A; FIG. 6D shows a side view illustrating the docking receptacle from an unrecessed side; and FIG. 6E shows a side view illustrating the docking receptacle from a recessed wall side of the device. Views from the sides opposite those shown in FIGS. 6D and 6E are identical.

FIG. 7A shows one perspective view of the core device from a curved front top wall perspective; FIG. 7B shows another perspective view of the core device rotated 180π from the view shown in FIG. 7A, shown from a flat top front watt perspective and illustrating an alignment boss in one core sidewall; FIG. 7C shows one bottom perspective view of the core device, shown from a flat top front wall perspective and illustrating the alignment boss in one core sidewall; FIG. 7D shows another bottom perspective view of the core device rotated 180° from the view shown in FIG. 7C, and shown from a curved front wall perspective; FIG. 7E shows a bottom view of the DED core device; FIG. 7F shows a top view of the DEL) core device; FIG. 7G shows a side view of the DED core device from a first sidewall perspective; FIG. 7H shows a side view of the DED core device from a second sidewall perspective rotated 90° from the view shown in FIG. 7G, and illustrating the boss in the second sidewall; FIG. 7I shows a side view of the DED core device from a third sidewall perspective rotated 90° from the view shown in FIG. 7H; and 7J shows a side view of the DED core device from a fourth sidewall perspective rotated 90° from the view shown in FIG. 7I.

It will be understood that the appended drawings are not necessarily to scale, and that they present one embodiment of many aspects of systems and components of the present invention. Specific design features, including dimensions, orientations, locations and configurations of various illustrated components may be modified, for example, for use in various intended applications and environments.

DETAILED DESCRIPTION OF EXEMPLARY EMBODIMENTS

Although specific embodiments of sensing assemblies are illustrated and described herein with reference to specific types of sensors, traces, carrier layers and terminals associated with particular substrates, it will be appreciated that similar fabrication techniques and features may be used with a variety of sensors, traces, terminals, carrier layers and substrates. In some embodiments, encapsulated sensor assemblies incorporating sensors, traces and terminals may be associated with footwear, footwear accessories or socks, as shown and described. In alternative embodiments, encapsulated sensor assemblies may be associated with various other types of garments (e.g. shirts, as shown and described, t-shirts, jerseys, shorts, pants, leotards, etc.), footwear (including shoes, boots, insoles, etc.) belts, straps, objects such as sporting equipment (e.g., shin guards and other protective gear), gloves, balls, bats, striking implements (e.g., rackets, clubs, and the like), grips (e.g., golf club grips, as shown and described, racket grips, steering wheel grips or covers, etc.), gaming implements and controllers, helmets, and the like. In some embodiments, sensor assemblies as disclosed herein may be associated with other types of substrates, such as upholstery (e.g., chairs, car seats, seat pads, postural accessories, etc.), sheets, medical devices and accessories, and similar items. The term "sensor," as we use it herein, refers to the various types of sensors as described herein, as well as additional sensors and means for sensing as that term may be construed to extend to sensors as described herein as well as other, additional types of sensors that may be associated with sensing assemblies and systems as described.

Figure 1A:
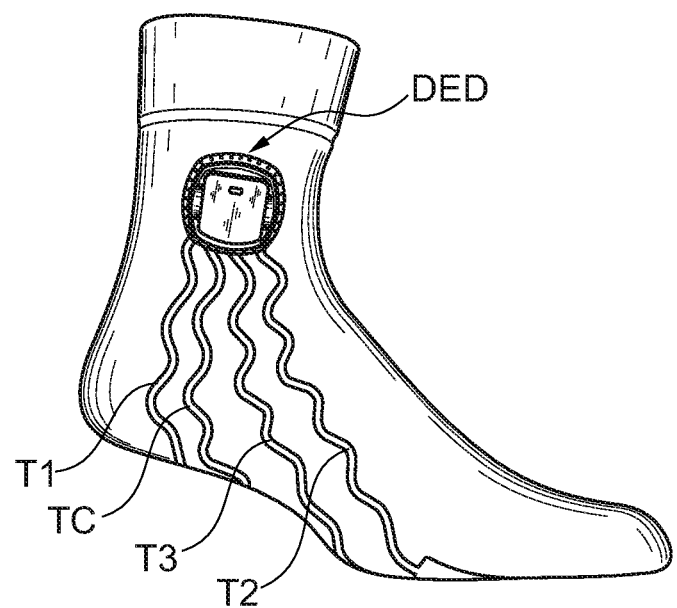
FIGS. 1A and 1B illustrate one embodiment of a sensor-enabled sock comprising a sensor assembly as described herein, wherein the sensor assembly comprises multiple sensors and multiple conductive traces encapsulated in (e.g., sandwiched between) two non-conductive carrier layers and associated with terminals provided in an SAS/DED combination.
Figure 1B:
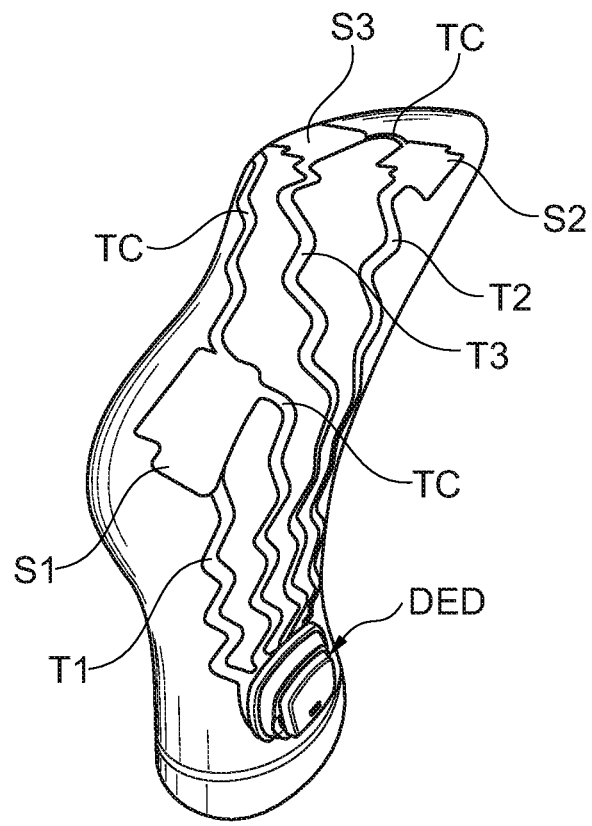

FIGS. 1A and 1B illustrate one embodiment of a sensor assembly as described herein, comprising multiple sensors and multiple conductive traces encapsulated in (e.g., sandwiched between) two carrier layers and associated with terminals provided in an SAS/DED combination, referenced as a DED. All sensor components are associated with a knit substrate in the form of a sock by association of the encapsulated sensor assembly and an SAS receptacle with the sock. FIG. 1A shows a side view of encapsulated conductive traces T1, T2, T3, TC terminating in an SAS/DED combination, referenced DED. FIG. 1B shows a perspective view of the bottom of the sock, illustrating a plurality of sensors S1, S2, S3, each sensor in operable communication with a corresponding conductive signal trace (T1, T2, T3, respectively) and a common trace TC, each of the traces terminating at the SAS/DED combination. Each sensor lead is coupled to two conductive traces, one signal pathway trace and one common trace.

Such sensor assemblies may be conveniently fabricated by creating a mask, positioning or applying desired sensors, (optional) leads, traces and/or terminals to the mask. The mask may comprise, for example, paper or polyester or another film. In some embodiments, a mask comprises a thin film having an adhesive surface on which sensor(s) and conductive traces may be positioned. In some embodiments, a mask may comprise a non-conductive woven or non-woven material to which sensor(s) may be affixed and, in some embodiments, conductive traces comprising conductive thread, yarn or fibers may be stitched to the mask. The mask may be cut (e.g., laser cut or die-cut) to a desired template configuration before or after application of the sensor assembly, or may remain in a sheet conformation for association with a carrier template.

In some embodiments, a desired carrier layer may be positioned on and associated with a mask and its associated sensor assembly, then matched with another carrier layer to provide an encapsulated sensor assembly. In some embodiments, desired sensors, (optional) leads, traces and/or terminals may be applied directly to a desired carrier layer without using a mask, and then matched with another carrier layer to provide an encapsulated sensor assembly. In some embodiments, mask and carrier layers may be pre-cut to a desired template configuration prior to application of the sensor assembly; in some embodiments, mask and/or carrier layers may be cut to desired template configurations following application of the sensor assembly.

Any desired sensor type, trace type, sensor location, trace pattern, and the like, may be assembled. The encapsulated sensor assembly may then be positioned on a substrate in the location and position desired and associated with the substrate, for example, by heat bonding, adhesive bonding, and other affixation techniques. In some embodiments, encapsulated sensor assemblies may be integrated in a substrate. These fabrication techniques can be adapted to providing sensor assemblies having a range of sensor types and positioning, trace types and positioning, and a wide range of terminal arrangements, suitable for use in a wide variety of applications, and different, specialized sensor assemblies and instrumented objects may be produced quickly and at low cost.

Figure 2A:
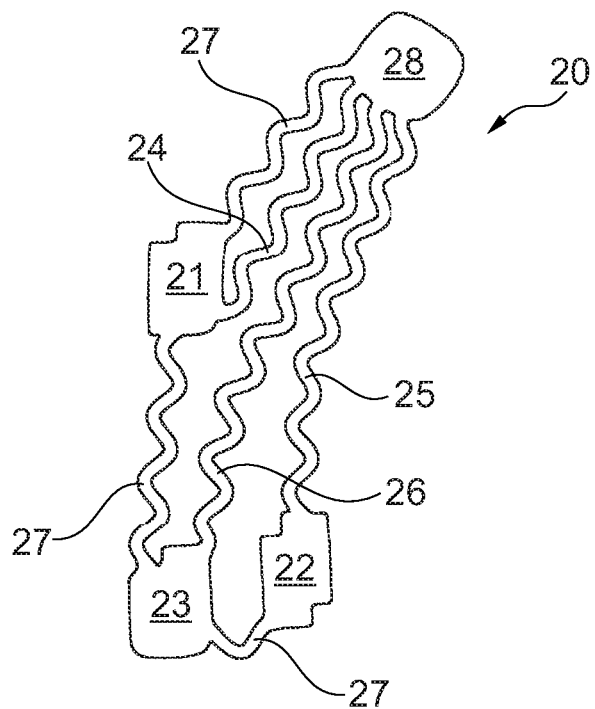
FIGS. 2A and 2B illustrate one embodiment of non-conductive carrier templates having a complementary, generally mirror-image configuration.
Figure 2B:
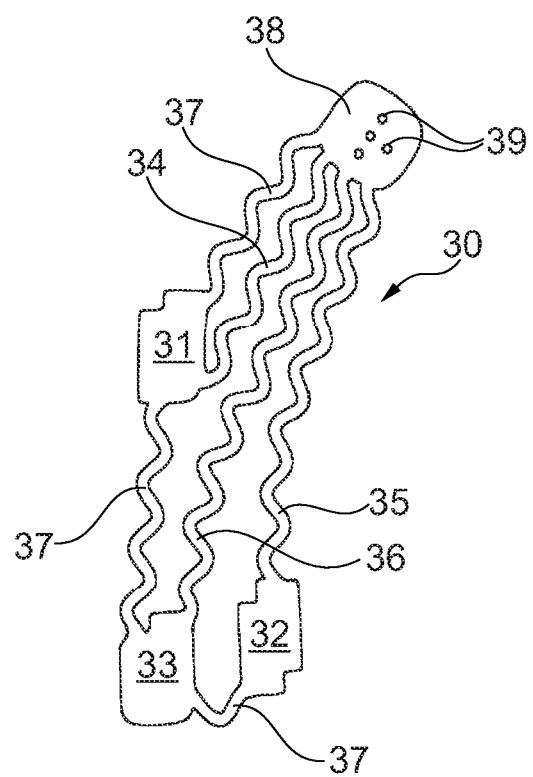

FIGS. 2A and 2B illustrate one embodiment of carrier templates 20, 30 having complementary, generally mirror-image configurations. Carrier template 20 shown in FIG. 2A is provided as a substrate interface carrier (for contacting an underlying substrate, such as footwear, a garment, an object, or the like) and comprises a plurality of sensor receiving locations 21, 22, 23, a plurality of sensor trace receiving pathways 24, 25, 26 corresponding to sensors S1, S2, S3, and a common or ground trace receiving pathway 27 connected to each of the sensor receiving locations serially. Carrier template 20 additionally comprises trace termination and SAS receiving location 28. The substrate interface carrier is generally associated with an underlying substrate (e.g., footwear, a garment or an object) by bonding or another affixation technique, or may be integrated in an underlying carrier.

FIG. 2B illustrates an electronics interface carrier template 30 complementary to carrier template 20 and configured for association with an SAS and/or DED having complementary terminal types and locations. Carrier template 30 comprises a plurality of sensor receiving locations 31, 32, 33, a plurality of sensor trace receiving pathways 34, 35, 36 corresponding to sensors S1, S2, S3, and a common or ground trace receiving pathway 37. Carrier template 30 additionally comprises trace termination and SAS receiving location 38 having a plurality of termination apertures 39.

Complementary carrier templates 20, 30 are designed to have a size and configuration that matches the size and configuration of a predetermined sensor assembly. In some embodiments, the size and configuration of carrier templates closely matches the size and configuration of a predetermined sensor assembly, so that the size and configuration of the sensor and trace receiving locations closely match the size and configuration of the sensors and conductive trace pathways. In some embodiments, a carrier template margin between a sensor or trace component and the edge of the carrier template is less than about 3 cm, in some embodiments, a carrier template margin is less than about 2 cm, and in some embodiments less than about 1 cm. It will be appreciated that sensor receiving locations may have a variety of sizes, configurations and locations, depending on the types of sensors implemented, and that trace receiving pathways may likewise have a variety of sizes, configurations, pathways and locations, depending on the type of conductive trace used, the sensor type and location, and the like. Trace receiving pathways may be provided as non-linear pathways, as shown, and may have an undulating, zig-zag or sinusoidal pattern, as shown.

Figure 3:
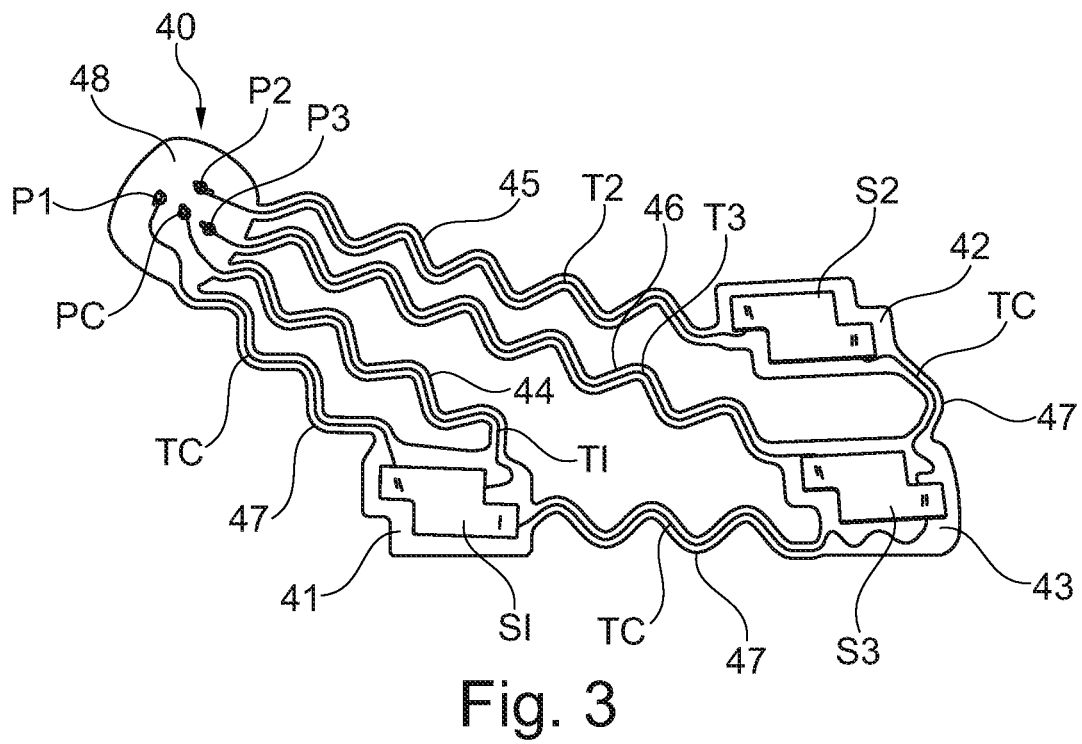
FIG. 3 illustrates a substrate interface carrier template having a plurality of sensors, a plurality of sensor traces and a common or ground trace associated with the carrier template and terminating at discrete terminal locations for connection to mating signal receipt terminations of an SAS or DED or SAS/DED combination.

FIG. 3 illustrates a substrate interface carrier template 40 having a plurality of sensors S1, S2, S3 associated with sensor receiving locations 41, 42, 43, a plurality of sensor traces T1, T2, T3 associated with trace receiving locations 44, 45, 46, and a common or ground trace TC associated with ground trace receiving pathway 47, serially connecting the sensors. Sensors S1, S2, S3 illustrated in FIG. 3 comprise an e-textile fabric, such as a pressure-sensing resistive e-textile fabric. Conductive sensor traces T1, T2, T3 and conductive trace TC illustrated in FIG. 3 comprise a conductive thread or yarn material that is operably coupled to the sensors by stitching or adhesive and transit undulating trace pathways to terminal locations. Conductive trace TC contacts each of the sensors serially and provides a conductive pathway to and/or from each of the sensors. Sensor and ground traces T1, T2, T3, TC terminate at discrete locations on trace termination and SAS receiving location 48. In the embodiment illustrated in FIG. 3, conductive termination posts P1, P2, P3, PC are associated with trace T1, T2, T3, TC terminations, respectively, for connection to mating signal receipt terminations. Conductive termination posts are electrically coupled to the trace terminations (and, thus, the respective sensors) and may be provided as electrically conductive pads, posts, epoxy drops, silicone glue, or the like.

Figure 4:
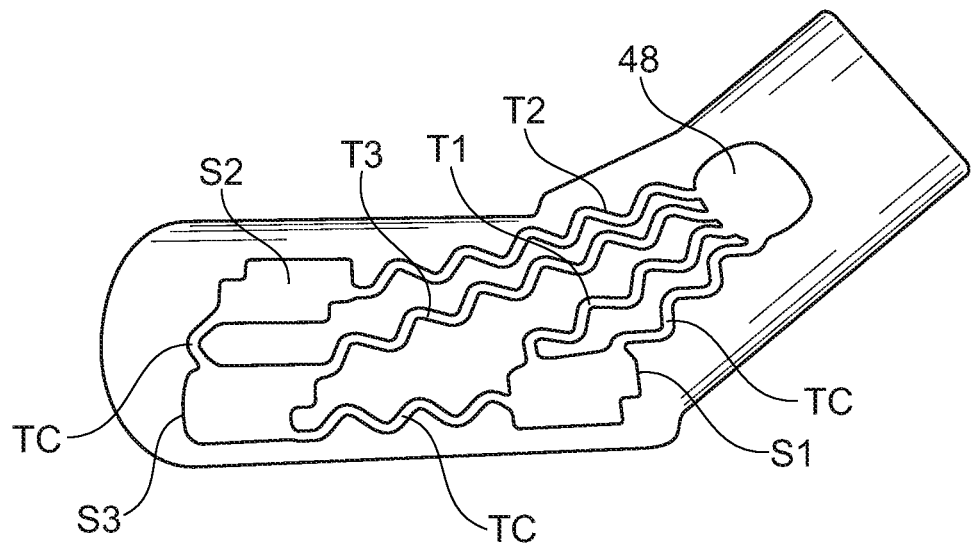
FIG. 4 illustrates a sensor assembly encapsulated between a substrate interface carrier template and a complementary electronics interface carrier template, with the substrate interface carrier mounted to a substrate (a sock).

An encapsulated sensor assembly may comprise a substrate interface carrier template having a sensor assembly as shown in FIG. 2A and an electronics interface carrier template as illustrated in FIG. 3 applied to encapsulate, or sandwich, the sensors and conductive traces between the carrier layers. The electronics interface carrier template as illustrated in FIG. 2B has a plurality of termination apertures 39 aligned for receiving and exposing conductive termination posts P1, P2, P3 and PC for communication with an electronics component. The sandwiched, or encapsulated sensor assembly may then be applied to (e.g., associated with) a substrate surface, such as the external surface of a sock, as shown in FIG. 4.

In some embodiments, one or more sensor(s) may comprise a pressure sensor capable of detecting levels of pressure (and/or force and/or shear or derivative measurements). Suitable pressure sensors may comprise resistive e-textile fabrics, resistive inks, resistive thermoplastic elastomers (TPE), resistive silicone-containing materials and a variety of other types of resistive materials. Thus, one or more of sensors S1, S2, S3, illustrated, may comprise an e-textile fabric sensor, a force-resistive (FSR) sensor, a resistive ink, a resistive TPE or silicone-containing material, or the like, and each of the sensors S1, S2, S3 may comprise different materials. Optional sensor leads for operatively connecting sensors to conductive traces/pathways may comprise the same material as the sensor or a different material, and conductive leads may be provided integrally with and/or in signal communication with sensor(s). In the embodiment illustrated in FIG. 3, sensor leads are provided as extensions of sensors S1, S2, S3, comprising the same material as the sensors. Conductive traces are in signal communication with leads and/or sensor(s) and provide conductive signal and/or common pathways between sensor(s) and signal transfer and/or common terminals (described below). Sensor assemblies may additionally include other types of sensors, including electrically conductive electrodes, vital sign monitoring sensors, accelerometers, gyroscopes, electromyography sensors, moisture sensors, and the like, forming a part of a sensor assembly as described, or separately associated with a substrate and sensing system.

Conductive traces may comprise conductive threads or yarns, conductive inks, conductive thermoplastic elastomers, conductive silicone-containing materials, and the like. Electrically conductive yarns, threads, fibers and fabric available under the mark X-STATIC are suitable and exemplary for fabricating conductive and common traces as described herein. The properties, compositions and characteristics of individual conductive traces may vary among traces, and may vary along the length of a single trace. In some embodiments, as illustrated in FIG. 3, conductive traces may be arranged in a zig-zag or sinusoidal or serpentine pattern.

Substrate and electronics interface carrier layers generally comprise a flexible, substantially electrically non-conductive and substantially moisture impermeable material. Electrically non-conductive carrier layers may comprise a sheet material that's flexible and may be at least somewhat stretchable. The term "sheet material," as used herein, refers to many types of pliable materials, including traditional flexible plastic sheeting material, pliable thermoplastic, foam and composite materials. In some embodiments, non-electrically conductive carrier layers may comprise a polyvinyl chloride (PVC) composition, a polyurethane (PU) composition, an elastomer composition, a natural or synthetic rubber composition, a silicone-containing composition, or a composition comprising another polymer having similar properties, plasticizers, or the like. Carrier layers are substantially non-electrically conductive and are preferably substantially liquid and moisture impermeable. In some embodiments, carrier layers having heat transfer properties are preferred. Heat transfer capabilities may provide bonding of the carrier layer to an underlying substrate; heat transfer capabilities may additionally or alternatively provide bonding of two carrier layers, or portions of two carrier layers, to one another. Carrier substrates that are easily weeded (capable of being cut to a predetermined or desired and complex configuration) are preferred. In one embodiment, substrate and electronics interface carrier layers comprise a PVC material that is highly stretchable such as Easyweed Stretch heat transfer vinyl by Siser.

Carrier layers are typically formed as thin membranes. Carrier layers having a thickness of from about 10 microns to about 0.5 mm may be suitable in some embodiments;

carrier layers having a thickness of about 40 microns are suitable for some applications; carrier layers having a thickness of about 85 microns are suitable for some applications; carrier layers having a thickness of about 150 microns are suitable for yet other applications. Complementary carrier layers may have different thickness, and one or both surfaces of a carrier layer may comprise an adhesive surface.

The carrier layer(s) may be bonded or adhered or otherwise affixed to a substrate material using heat bonding techniques, adhesive materials, or other types of bonding techniques, to provide secure positioning of the substrate interface carrier layer and sensor assembly on the substrate. In heat bonding applications, the carrier layer preferably has an application temperature (at which the carrier layer bonds to the substrate) of from about 60° C. to about 200° C.; in some embodiments the application temperature is about 150° C. In embodiments using multiple carrier layers, the carrier layers may additionally be bonded or adhered or otherwise affixed to one another to securely position (e.g., sandwich) the sensor(s) and any associated components intermediate multiple carrier layers.

The prototype sensor assembly is illustrated in FIG. 4 applied to a sock substrate, with the sensors S1, S2, S3 positioned at plantar locations, sensor S1 located at a plantar heel calcaneus location, sensor S3 positioned at a plantar first metatarsal head region of the sock, and sensor S2 positioned at a plantar fifth metatarsal head region of the sock. The (signal pathway and common) traces are routed to a common location, and may be routed along side-by-side pathways, sandwiched between continuous carrier layers, and coupled to signal transfer terminals P1, P2, P3, PC.

The projecting signal transfer and common terminals, provided as conductive posts as shown in FIG. 3, may operatively connect to an electronics device provided on a non-conductive mounting tab or in a non-conductive SAS element. External surfaces of signal transfer and common posts are provided as shaped conductive terminals that couple to mating signal and common receipt terminals in an SAS, SAS/DED combination or DED that can be operably connected to the trace terminals. Different types of signal transfer and common terminations and hardware may be implemented.

Figure 5A:
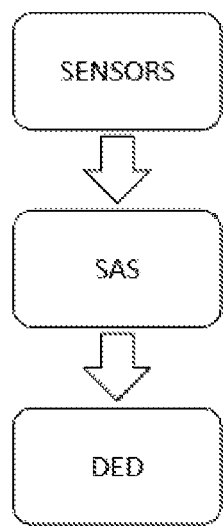
FIGS. 5A and 5B show schematic diagrams illustrating SAS and DED components operatively coupled to sensors.
Figure 5B:
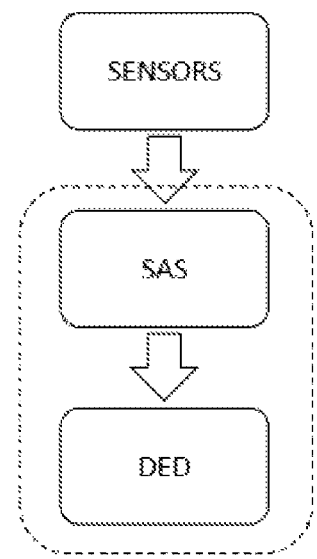

FIGS. 5A and 5B show schematic diagrams illustrating SAS and DED components operatively coupled to sensors. FIG. 5A schematically shows an embodiment in which sensors are operatively coupled to a discrete SAS component, and the discrete SAS component is operatively coupled to a discrete DED component. FIG. 5B schematically shows an embodiment in which sensors are operatively coupled to an electronic component providing both SAS and DED functions.

Figure 6A:
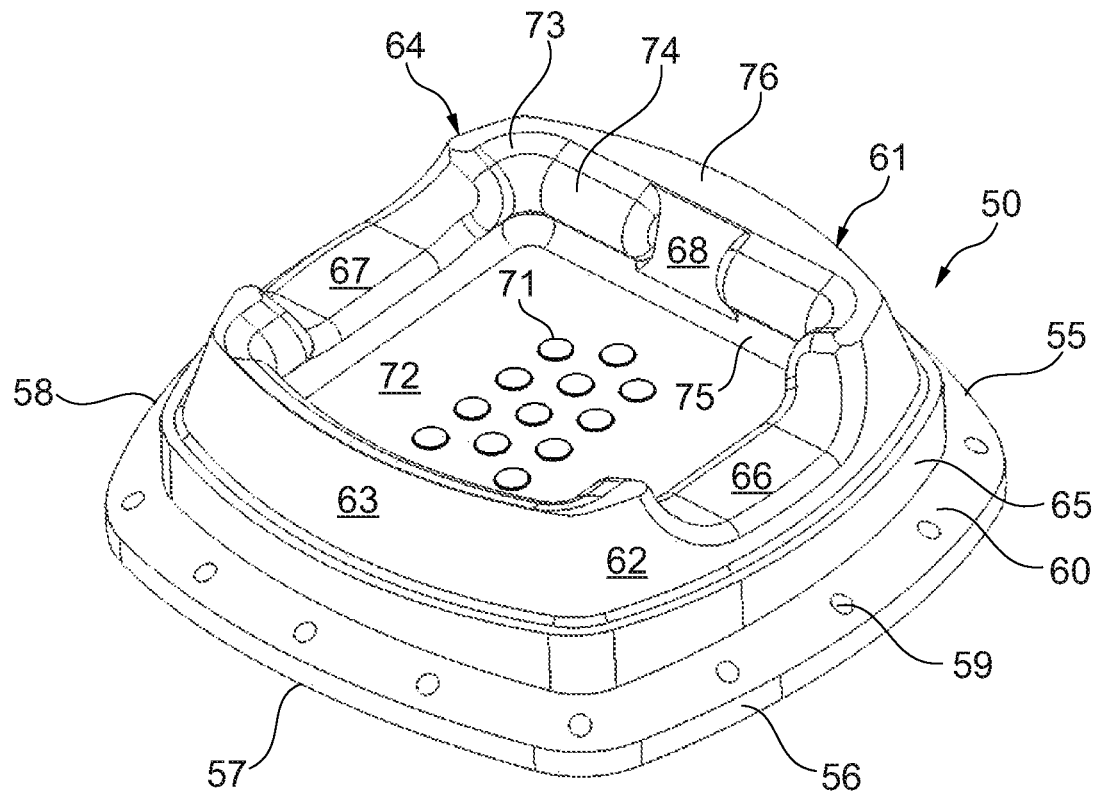
FIGS. 6A-6E show various views of one embodiment of an SAS docking receptacle as disclosed herein.
Figure 6B:
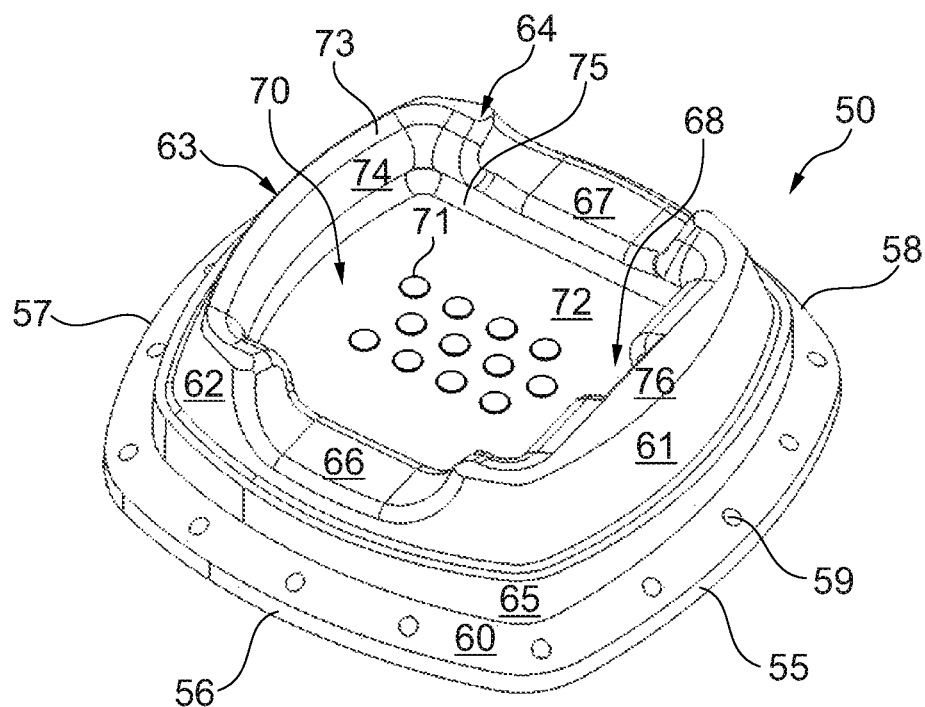
Figure 6C:
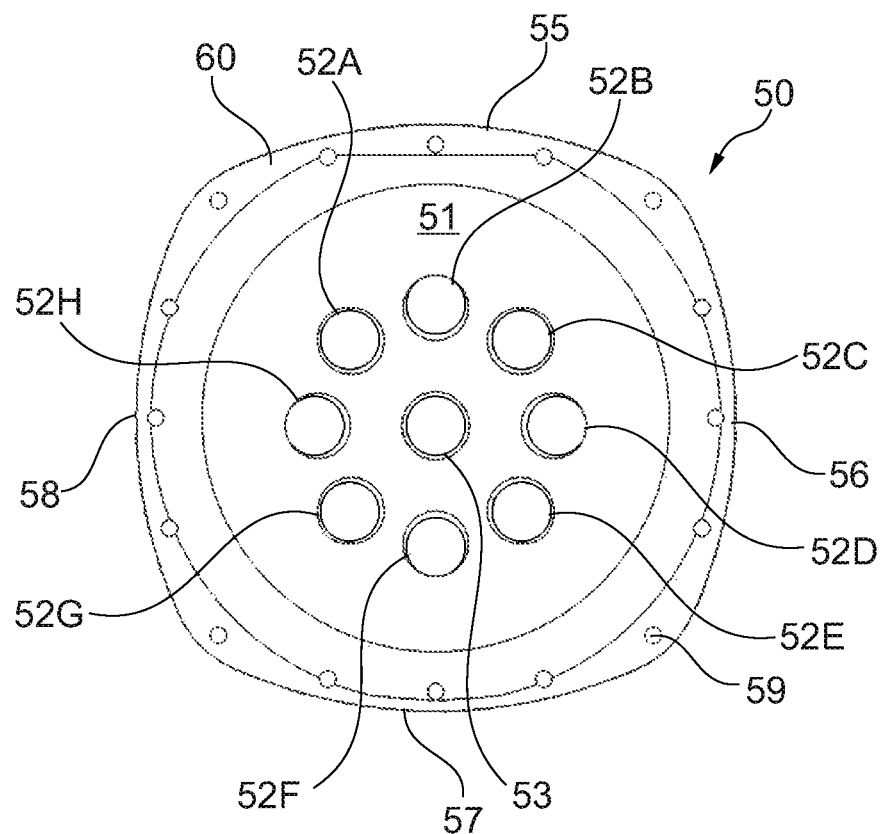
Figure 6D:
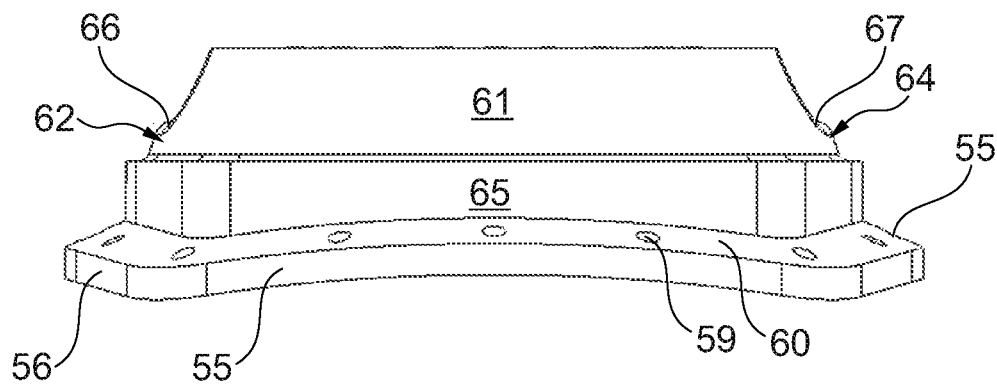
Figure 6E:
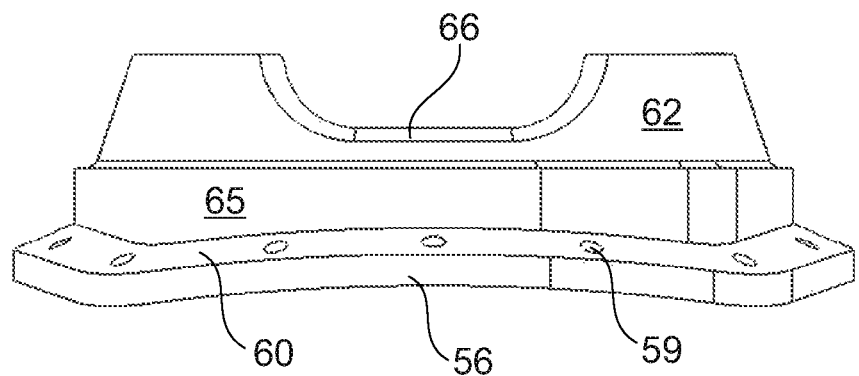
Figure 7A:
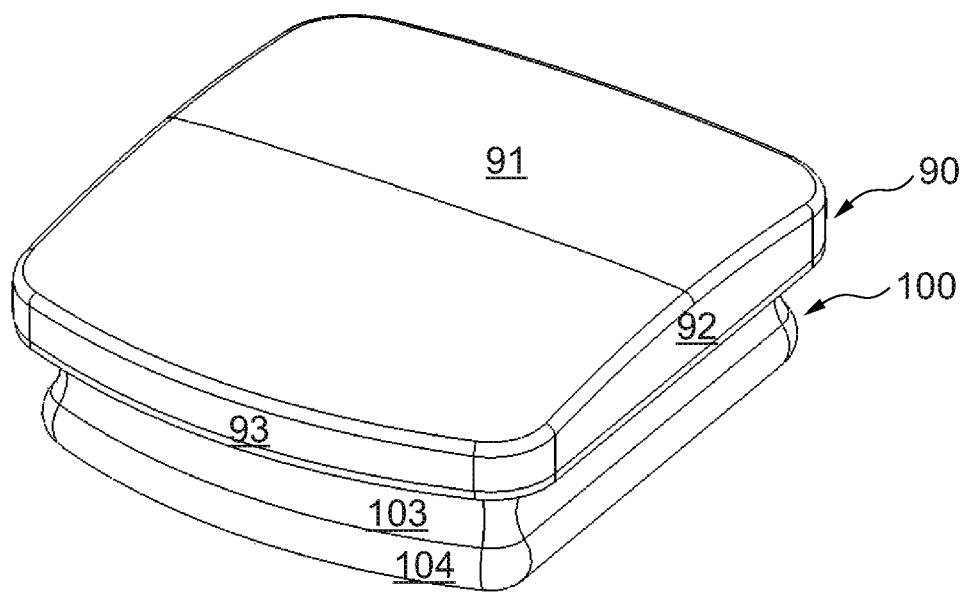
FIGS. 7A-7J show various views of one embodiment of a DED core device as disclosed herein, suitable for mating with the SAS docking receptacle illustrated in FIGS. 6A-6E.
Figure 7B:
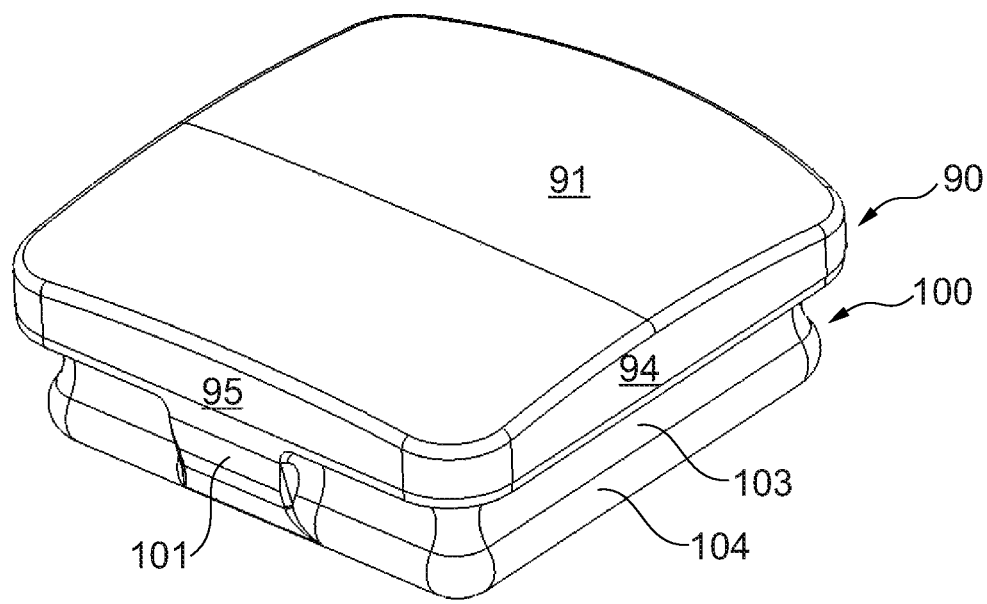
Figure 7C:
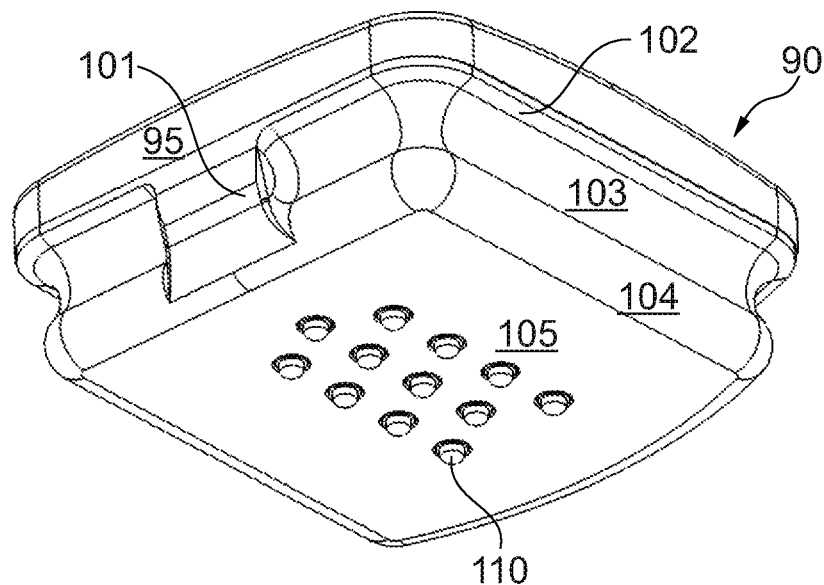
Figure 7D:
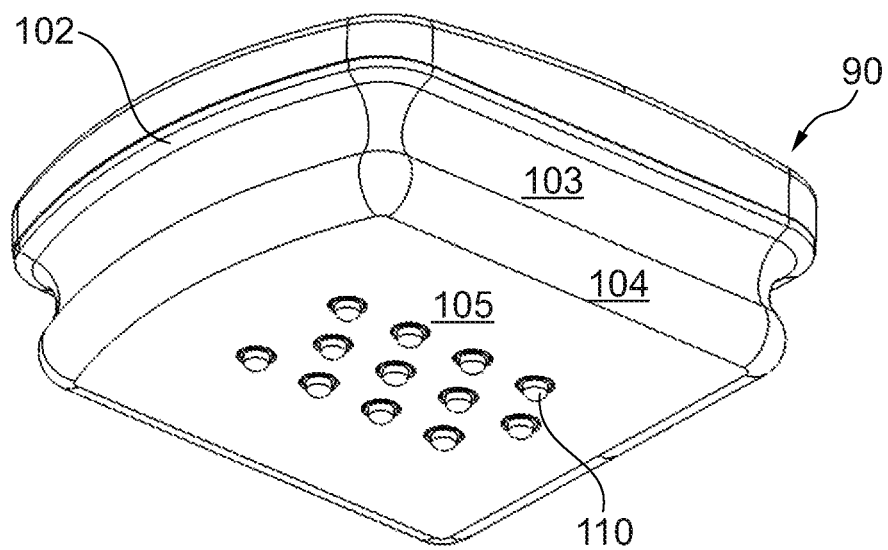
Figure 7E:
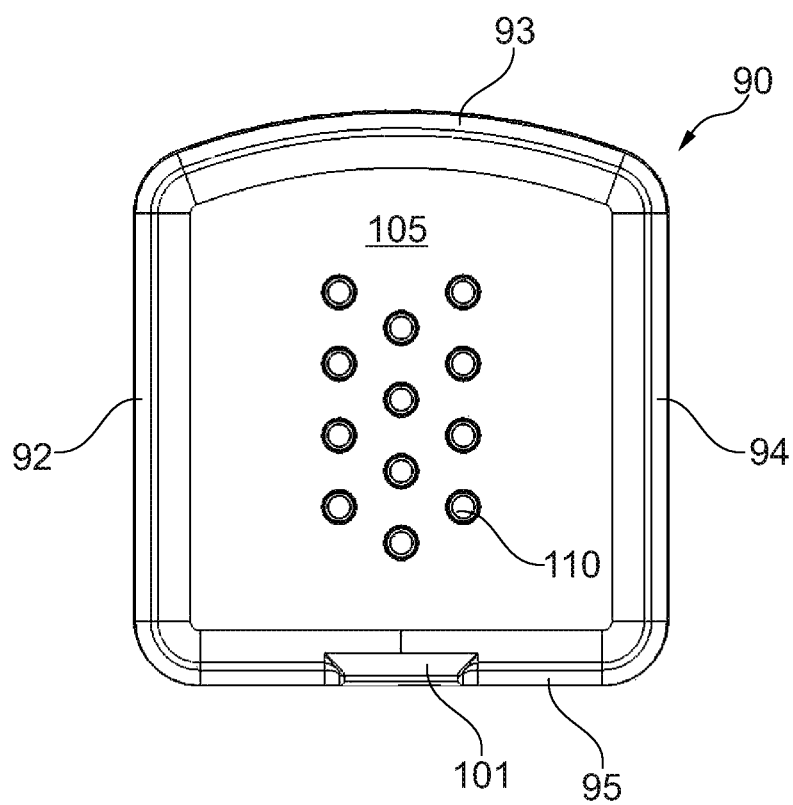
Figure 7F:
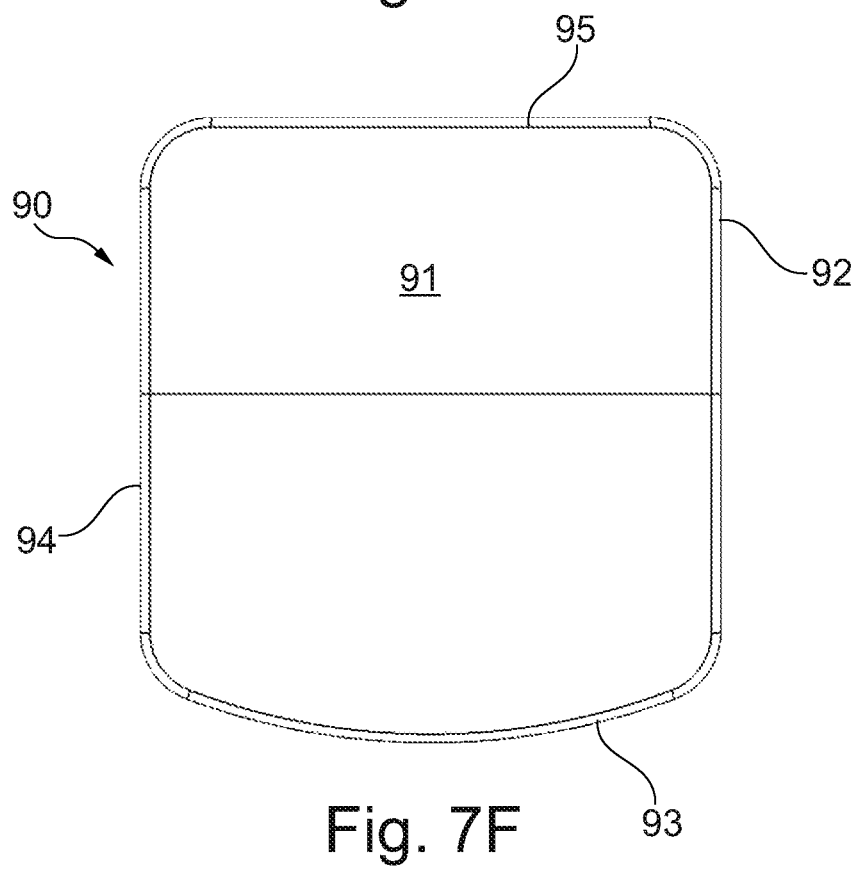
Figure 7G:
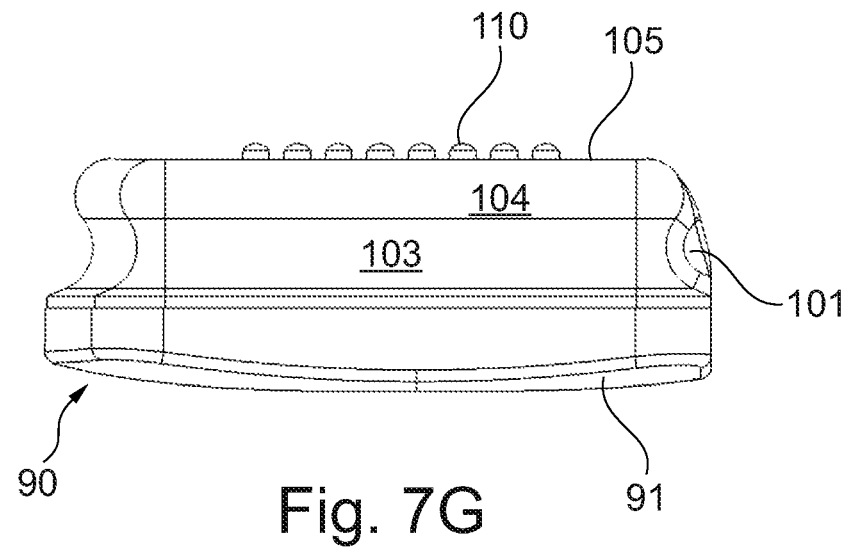
Figure 7H:
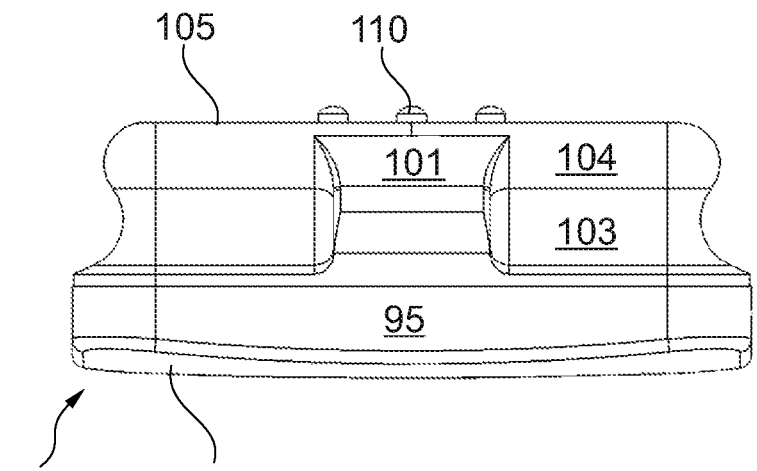
Figure 7I:
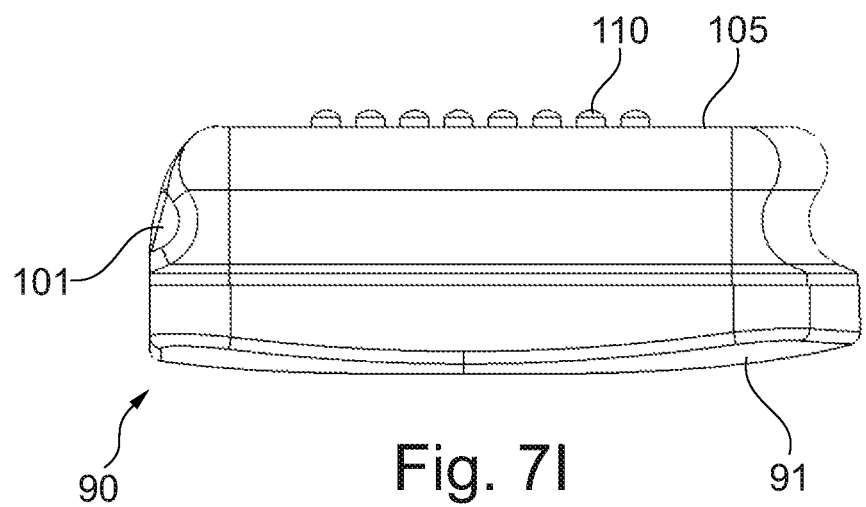
Figure 7J:
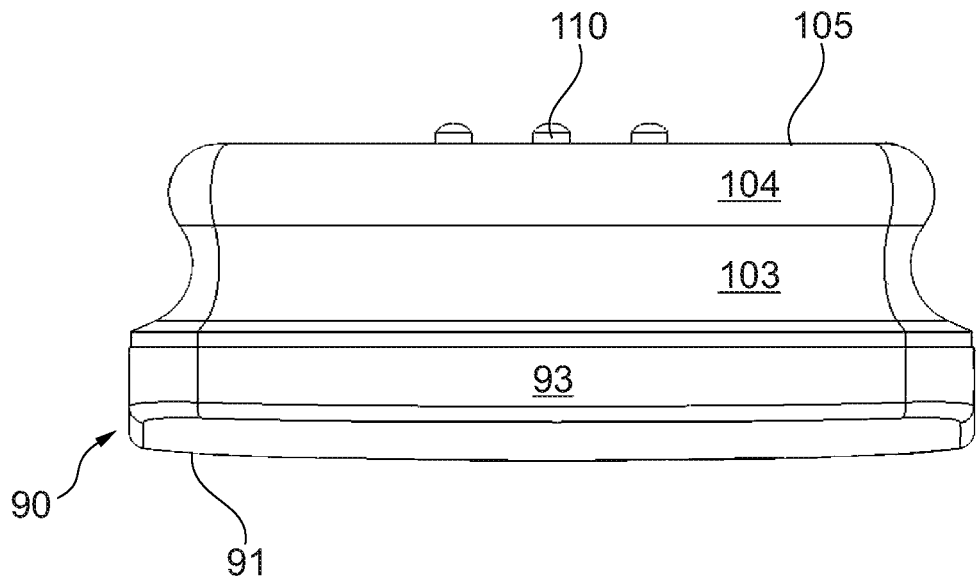

FIGS. 6A-6E show various views of one embodiment of an SAS docking receptacle as disclosed herein. FIG. 6A shows one top perspective view of the device illustrating the contours of the docking receptacle and showing an alignment recess provided in one internal receptacle sidewall; FIG. 6B shows another top perspective view of the device of FIG. 6A rotated 90° from the perspective shown in FIG. 6A; FIG. 6C shows a bottom view of the device of FIG. 6A illustrating conductive pads for contacting termination posts associated with a sensor-enabled garment or object; FIG. 6D shows a side view illustrating the docking receptacle showing an unrecessed sidewall; and FIG. 6E shows a side view illustrating the docking receptacle showing a recessed sidewall of the device, rotated 90° from the view shown in FIG. 6D. Views from the sides opposite those shown in FIGS. 6D and 6E are identical.

FIGS. 6A and 6B illustrate perspective views of the DED core receiving structure of one embodiment of an SAS docking receptacle 50 as described herein, configured for securely receiving and electrically interfacing with a DED core device such as illustrated in FIGS. 7A-7J. The DED interface surface of the SAS docking receptacle is contoured for mechanical mating with a mating DED structure, and presents a plurality of exposed conductive signal terminals and a plurality of exposed auxiliary terminals for operably (e.g., electrically) coupling to mating terminals in a DED core device. The SAS docking receptacle and DED core device provide sealed housings for various electrical and electronics components and may additionally comprise one or more sensors, data storage devices, signal processing and/or analysis devices, and other types of programmed and/or programmable devices. The SAS docking receptacle and DED core device housings are generally fabricated from a substantially non-electrically conductive and moisture impermeable material, such as a plastic material, a thermoplastic elastomer, a natural or synthetic rubber material, or the like.

FIG. 6C shows a bottom view of SAS docking receptacle 50 comprising a sensor assembly terminal interface surface 51 having a plurality of exposed conductive terminals 52A-52H and a common or ground conductive terminal 53. Conductive terminals 52A-H and 53 are configured and arranged for operable connection to one or more exposed terminals at the substrate interface, such as terminal posts P1, P2, P3, PC as illustrated in FIG. 3 and may comprise conductive pads that are flush with terminal interface surface 51, or that project slightly from terminal interface surface 51. The number and arrangement of conductive terminals on terminal interface surface 51 may be configured to match the number and arrangement of exposed terminals at a substrate interface providing communication with any particular sensor assembly. In the embodiment shown in FIG. 6C, the arrangement of SAS docking receptacle conductive terminals 52A-52H corresponds to the arrangement of conductive sensor assembly posts illustrated in FIG. 3, and this SAS docking receptacle may therefore be matched with a sensor assembly as illustrated in FIG. 3. Additional conductive terminals are provided in the SAS docking receptacle to provide additional capability to provide a common SAS docking receptacle that may be used with a variety of sensor assemblies associated with a variety of garments, objects and footwear. While the conductive terminals provided in the SAS docking receptacle are shown in a circular configuration and a single, central common terminal is provided, it will be appreciated that any number of conductive and common or ground terminals arranged in a variety of arrangements may be provided in the SAS docking receptacle.

Peripheral docking receptacle side walls 55, 56, 57, 58 in the embodiment illustrated in FIG. 6C are slightly curved and interface with one another at curved corners, forming a generally square peripheral configuration. Bores or apertures 59 are optionally provided in a peripheral area of terminal interface surface 51 to facilitate association of SAS docking device 50 to an underlying substrate via stitching, grommets, pins or the like that penetrate apertures 59. Terminal interface surface 51 may be substantially planar, as shown, or it may be curved or have a three-dimensional configuration, in each case designed to match the three-dimensional configuration of an underlying garment or object.

FIGS. 6A and 6B show drawings illustrating SAS docking receptacle component including a DED core receiving cavity 70 having a plurality of contacts such as conductive pins 71 penetrating an internal base wall 72 in a contact interface region for mating with complementary contacts on a mating DED core device. In the embodiment illustrated in FIGS. 6A and 6B, conductive pins 71 comprise a plurality of sensor channels and one of more auxiliary channels, such as one or more common or ground channels, one or more energy or signal transfer channels for transferring energy or signals between the DED core and SAS docking devices). Each conductive pin 71 providing a sensor channel is in operable contact with a conductive terminal (52A-H) provided on the SAS docking terminal interface surface 51, and each conductive pin providing a common or ground channel is in operable contact with a conductive ground terminal 53 provided on the SAS docking terminal interface surface 51. Each SAS core pin providing a sensor channel is thereby in operable communication with a discrete sensor trace and sensor provided in a sensor assembly with which the SAS is associated, and each SAS core pin providing a common or ground channel is in operable communication with a discrete ground or common trace provided in a sensor assembly. In some embodiments, one or more conductive pin(s) 71 penetrating internal SAS base wan 72 may be operably connected to one or more sensors provided in the SAS docking device itself, providing a signal pathway from an SAS sensor to the DED core device.

In the embodiments illustrated herein, the upper and side wall contours of receipt cavity 70 correspond generally to outer contours of a DED body, as shown in FIGS. 7A-7J, to provide detachable yet stable mounting of DED core device 90 in receipt cavity 70. SAS docking receptacle comprises a plurality of side walls 61, 62, 63, 64 extending away from a base wall 60. Exterior surfaces of side walls 61, 62, 63, 64 may be tapered or radiused, as shown, toward a central location. A peripheral rim 65 having a different peripheral dimension (larger, as shown) than the peripheral dimensions) of side walls 61, 62, 63, 64 forming the receipt cavity 70 may be provided intermediate the base wall 60 and side walls 61, 62, 63, 64, as shown.

In the illustrated embodiment, two opposing side walls (61, 63, as shown) may have a substantially continuous outer surface, while two opposing side walls (62, 64 as shown) may have recessed areas defined by recess walls 66, 67 (shown as U-shaped walls) providing access from exterior surfaces of SAS side walls to receipt cavity 70. An interior surface of one or more of the side walls (side wall 61, as shown) may have an alignment cavity 68, sized and configured for mating with a complementary alignment boss provided on a mating DED core device. It will be appreciated that alignment cavities may have different sizes, configurations and placements, depending on the configuration of the SAS docking and DED core devices. Interior side wall configurations of SAS receipt cavity 70 may have a curved configuration, as shown, with upper chamfered peripheral surfaces 73, central curved surfaces 74 and a chamfered base wall interface surface 75. In some embodiments, an enlarged and flattened top wall 76 may be provided at one or more side wall locations. In the illustrated embodiment, flattened top wall 76 is provided as the upper surface of side wall 61.

Specific DED core embodiments are illustrated in FIGS. 7A-7J. DED core device 90, as illustrated, comprises an exterior surface 91 interfacing with side walls 92, 93, 94, 95. In the embodiment illustrated, the configuration of DED exterior surface is generally rectangular, having a rounded polygonal peripheral configuration with three substantially flat peripheral edges interfacing with side walls 92, 94, 95 and one curved peripheral edge interfacing with side wall 93. Exterior surface 91 may display optional indicators such as indicators such as visual indicators (e.g., LEDs) for communicating various system operational conditions, charge status, operational status, and the like. Exterior surface 91 may carry additional or different user interface features, actuators, displays, decorative matter, and the like. Exterior surface 91, as illustrated, has a perimeter larger than that of DED body 100, forming an enlarged rim extending peripherally of side walls 92, 93, 94, 95. The conformation of exterior surface 91 may be substantially flat, or it may have a curved or another three-dimensional configuration, and the surface may be smooth or textured or contoured. Side walls 92, 93, 94 95 are illustrated as being generally flat with chamfered surfaces interfacing with exterior surface 91; in alternative embodiments, side walls 92, 93, 94, 95 may be curved or have another three-dimensional configuration.

DED core body 100 comprises side walls having a configuration that is complementary to and matches side walls of the SAS receptacle receipt cavity 70, providing a secure press-fit of DED core body 100 in SAS receipt cavity 70. In the embodiment illustrated, DED core boss 101 is sized, located and configured to align and mate with alignment cavity 68 provided in the SAS receipt cavity. DED core side walls 102, 103, 104 are likewise sized, located and configured to securely contact upper chamfered peripheral surfaces 73, central curved surfaces 74 and a chamfered base wall interface surface 75 of the SAS receipt cavity. DED core base wall 105 is likewise sized, located and configured to align with and contact SAS receptacle internal base wall 72, and DED core contacts 110 are sized, located and arranged to align with and contact conductive pins 71 penetrating the SAS receptacle internal base wall 72. In some embodiments, DED core contacts 110 project from DED core base wall 105 and comprise, for example, fixed conductive posts or pins, spring-loaded posts or pins such as pogo pins, or the like. Magnetic and other types of contacting connections may be used.

Figure 8:
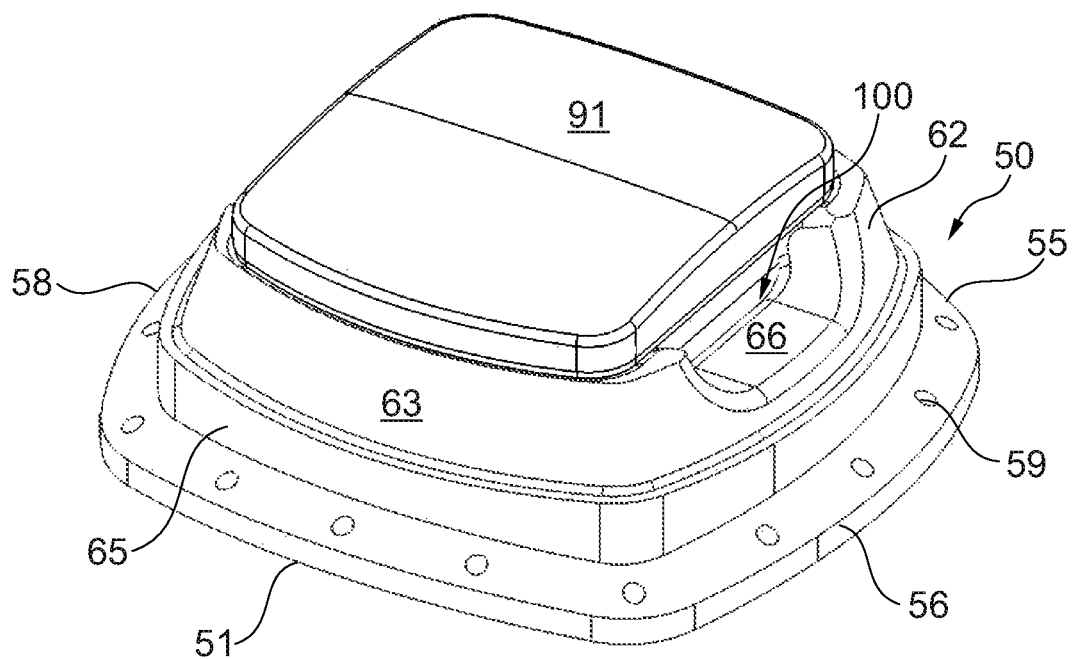
FIG. 8 shows a top perspective view of the DED core device of FIGS. 7A-7J mated in the SAS docking receptacle illustrated in FIGS. 6A-6E.

FIG. 8 illustrates a DED core device 90 as illustrated in FIGS. 7A-7J mounted in an SAS docking receptacle 50 as illustrated in FIGS. 6A-6E. DED core body 100 is substantially enclosed within SAS receipt cavity 70 in a substantially sealed manner. Tapered external side walls and upper rims of the SAS receptacle are sized and configured to align with and contact complementary side walls of the DED core device. Recessed areas defined by SAS recess walls 66, 67 provide handholds for a user to securely grip an enlarged exterior rim of the DED core device for conveniently detaching the DM core device from the SAS docking receptacle. While DED core device 90 and SAS docking receptacle 50 are illustrated having a generally square perimeter, it will be appreciated that other configurations may be used, including circular, oblong, other polygonal configurations, and other curved configurations. It will also be appreciated that while a snap-in type of interface between DED core device 90 and SAS docking receptacle 50 is illustrated, other types of interface arrangements may be implemented, such as sliding fixtures, magnetic fixtures, and the like. SAS docking receptacles and DED core devices having different configurations and sizes may be designed to interface with a variety of sensor systems embodied in different types of footwear, garments, objects and other types of substrates. The type of sensor(s), garment(s), substrate(s), placement of sensor(s), DED, conductive terminal(s), and the like, may be varied for use in many different sensor system applications.

DED core and SAS docking receptacle device housings are generally constructed from a flexible, bendable non-conductive material such as a non-conductive, flexible thermoplastic elastomer (TPE), silicone, or the like. Alternatively, SAS and/or DED core device or device components may be constructed from harder, more rigid non-conductive and substantially moisture resistant materials, and either or both SAS and/or DED core devices may house electrical and electronic components such as one or more accelerometer(s); one or more gyroscope(s); one or more magnetometer(s); one or more 6-axis and/or 9-axis inertial measurement units IMU(s); electronic components configured for data processing, data storage (e.g., flash memory), data communications Bluetooth, ANT+, Wi-Fi; and/or Proprietary TX/RX protocols) or the like; energy source(s) (e.g., rechargeable battery/ies, energy harvesting modules, and the like); antenna/e for wireless communications; and a plurality of analog sensor inputs (for pressure, temperature, humidity, altitude, and other sensor parameters).

In some embodiments, an SAS docking and/or DED core device may be provided as sensor and data acquisition devices in and of themselves, without connection to a sensor assembly associated with an underlying substrate. In these embodiments, an SAS or DED device, or an SAS/DED combination may comprise one or more sensors, such as sensors for sensing temperature, humidity, altitude, location, or the like, one or more accelerometer(s); one or more gyroscope(s), one or more magnetometer(s); one or more 6-axis and/or 9-axis inertial measurement units IMU(s); electronic components configured for data processing, data storage (e.g., flash memory), data communications (e.g., Bluetooth, ANT+, Wi-Fi; and/or Proprietary TX/RX protocols) or the like; energy source(s) (e.g., rechargeable battery/ies, energy harvesting modules, and the like); antenna/e for wireless communications; and other electronic and communications devices. Sensors may be provided in an SAS device associated with a substrate and/or in a DED device, and one or both of the SAS and DED may be permanently or detachably attachable to an underlying substrate (e.g., footwear, garment, object, etc.). In some embodiments, an SAS docking device may be associated with a substrate and provide a "dumb" docking device for detachably mating with a DED having sensing, data processing and/or storage and communications capabilities. In some embodiments, an SAS docking device having sensing and/or data processing and/or storage capabilities and data transfer terminals may be provided and associated with a substrate for detachably mating with a DED having sensing and/or data processing and/or storage and communications capabilities.

Figure 9:
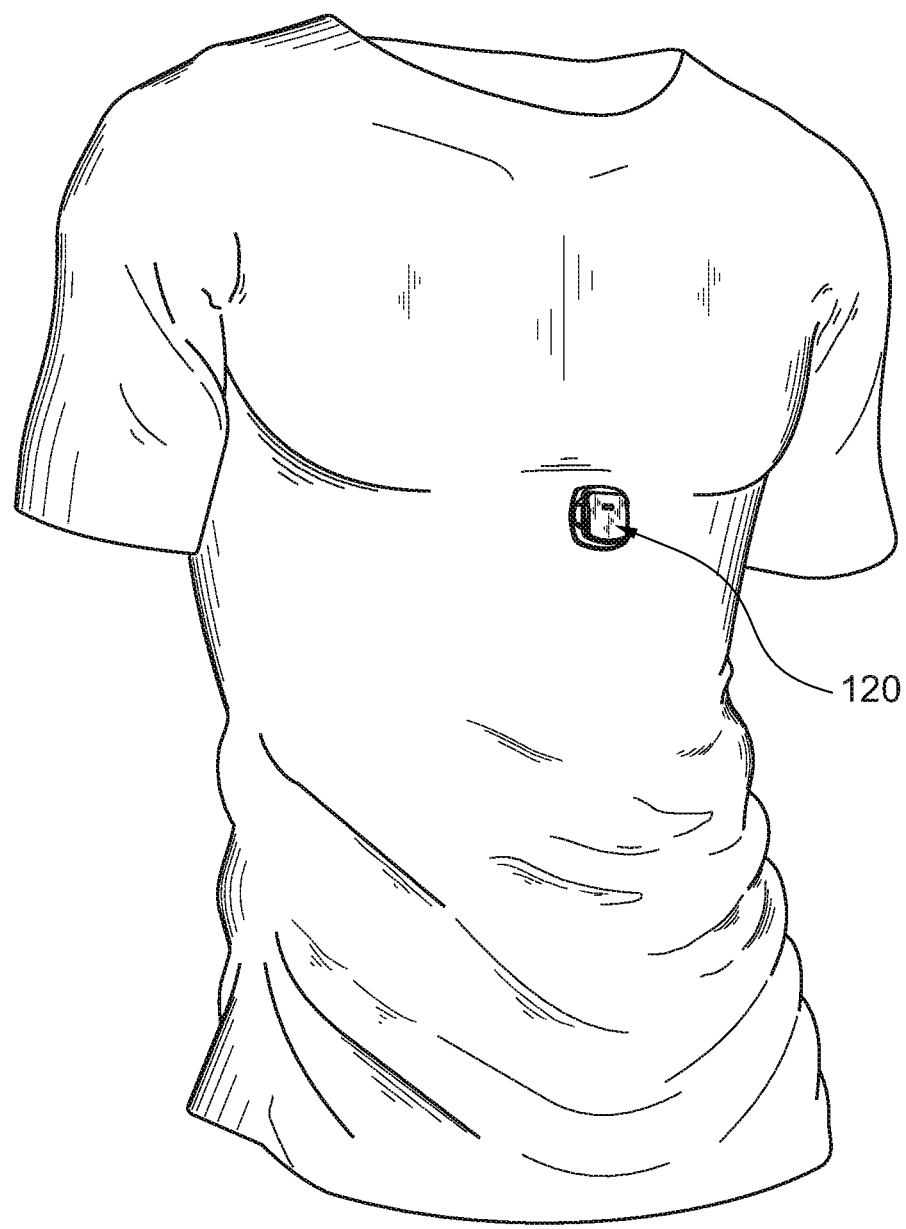
FIG. 9 illustrates one example of an SAS/DED receptacle/core combination mated and mounted on a T-shirt, optionally operatively coupling with sensors located on or in the T-shirt (not shown).

FIG. 9 illustrates one embodiment of an SAS and DED combination 120 associated with a garment—a shirt, as shown. In this exemplary embodiment, the housing of the SAS docking device may be permanently or detachably associated with the garment. In some embodiments, the SAS docking device may be configured for use with an uninstrumented garment and provide a "dumb" docking device for detachably mating with a DED having sensing, data processing and/or storage and communications capabilities. In some embodiments, the SAS docking device is configured for operable connection to a sensor assembly associated with the garment, such as a sensor assembly provided on inner surfaces of the garment (not shown). In some embodiments, the SAS docking device may itself serve as the sensing assembly, and may carry one or more sensors and associated terminals. The DED mates with and connects to the SAS on the garment by means of a mating mechanism such as that described above.

In some embodiments, the sensor assemblies provided in association with a garment may comprise e-textile or traditional pressure sensors capable of detecting levels of pressure (and/or force and/or shear or derivative measurements such as respiration rate) at one or more areas of the torso, electrically conductive electrodes monitoring biometric data such as heart rate and ECG, muscle activation, galvanic skin response, dehydration level and the like, and may include additional sensors, accelerometers, gyroscopes, electromyography sensors, moisture sensors, and the like. In the embodiment illustrated in FIG. 9, the SAS docking device may be positioned centrally at the front of a t-shirt, as shown, or in other locations of the t-shirt.

Figure 10A:
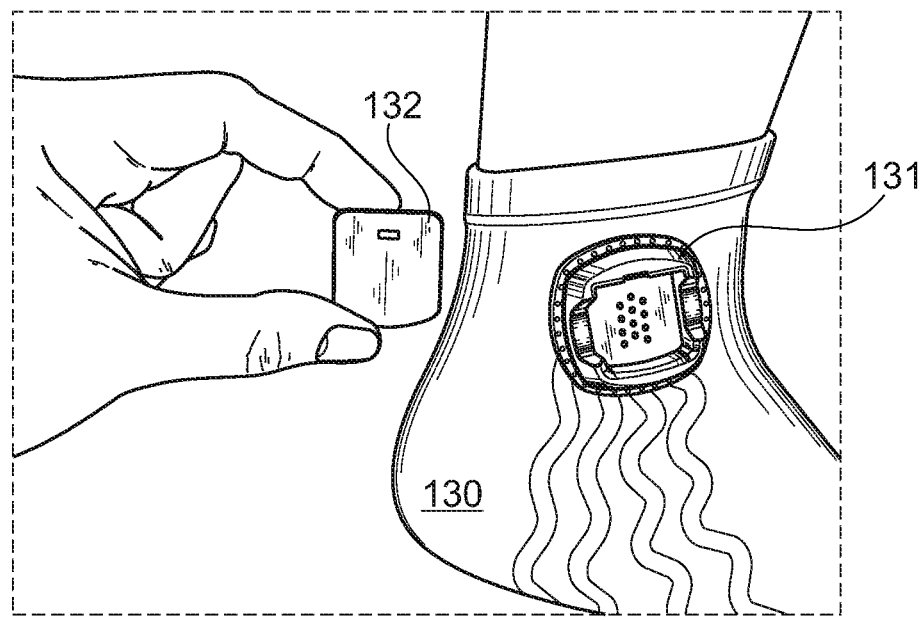
FIG. 10A shows one embodiment of an SAS receptacle mounted on a sock and operatively connected to sensors provided in the sock via conductive traces, with a DED component configured to be received in the SAS receptacle.
Figure 10B:
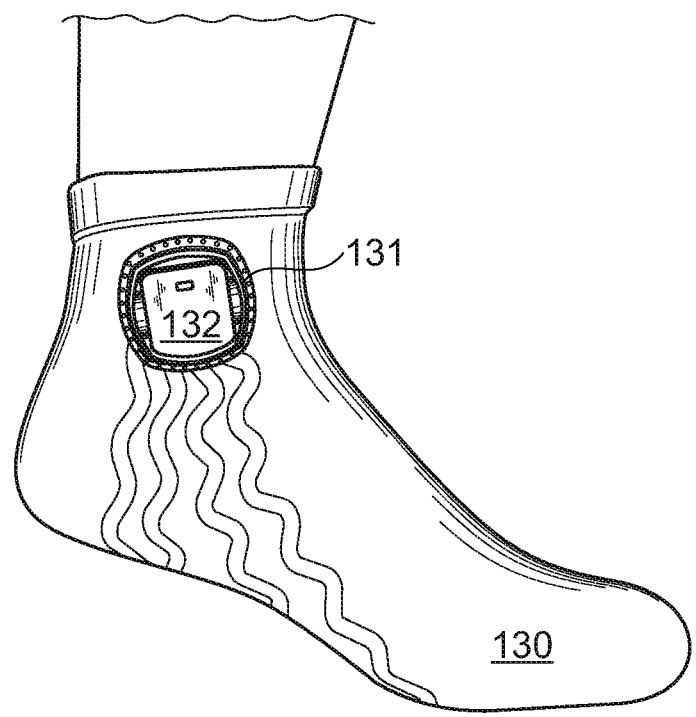
FIG. 10B illustrates the DED component mounted in the SAS, both electronic components mounted on the outer surface of the sock.

FIGS. 10A and 10B illustrate a sock prototype incorporating a sensor assembly and an SAS docking device for mating with a DED core. FIG. 10A illustrates a sock 130 having a plurality of conductive traces communicating with sensors located elsewhere on the sock and terminating at an associated SAS docking device 131. A separate DED core 132 is configured for mating with and operably coupling to the SAS docking device 131, providing signal and/or data communication between the sensor assembly, SAS docking device and DED core. In this exemplary embodiment, SAS docking device 131 is associated at the ankle level of the sock. Sensors, positioned on or in the sock, may be connected to the SAS via connections of different kinds, including traditional wiring, e-textile conductive traces, conductive inks/glues and/or mating elements such as connectors. In this exemplary embodiment, sensors used in sock applications may comprise e-textile pressure sensors capable of detecting levels of pressure (and/or force and/or shear or derivative measurements) at one or more areas of the foot and may include other types of sensors, including electrically conductive electrodes, vital sign monitoring sensors, accelerometers, gyroscopes, electromyography sensors, moisture sensors, and the like.

Figure 11A:
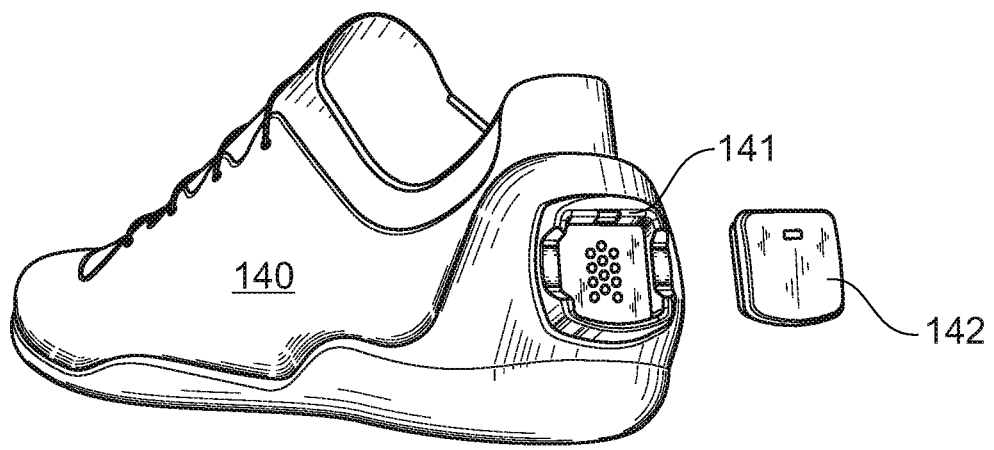
FIG. 11A shows one embodiment of an SAS receptacle mounted on a shoe and operatively connected to sensors provided in the shoe via conductive traces with a DED component configured to be received in the SAS receptacle.
Figure 11B:
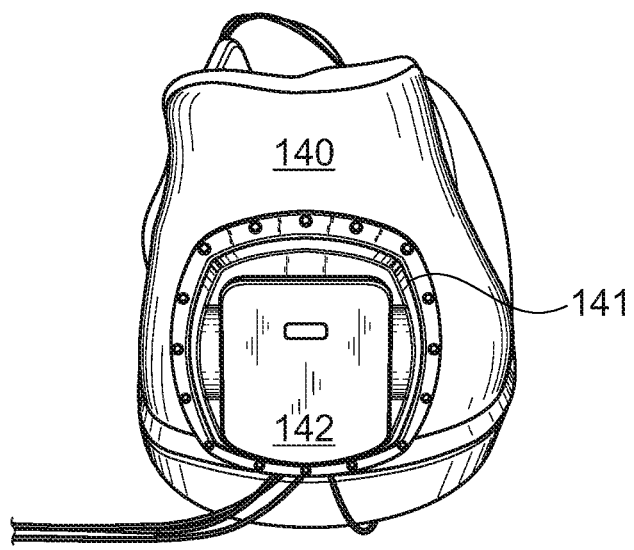
FIG. 11B illustrates the DED component mounted in the SAS, both electronic components mounted on the heel of a shoe.

FIGS. 11A and 11B illustrate an embodiment of an SAS docking device 141 associated with a running shoe 140 and configured for mechanically and electrically mating with a complementary DED core device 142. In this exemplary embodiment, the SAS docking device 141 is mounted on the back of the shoe. The DED core may mate to the SAS dock using a mating mechanism such as the mechanical mating arrangement described above. Sensors, associated with a shoe component, such as a shoe upper, insole, tongue, liner, padding, or the like, may be connected to the SAS docking device via various types of conductive pathways, such as traditional wiring, e-textile conductive traces, conductive yarns, threads or fibers, conductive inks/glues and the like. In this exemplary embodiment, sensors may comprise e-textile or traditional pressure sensors capable of detecting levels of pressure (and/or force and/or shear or derivative measurements) at one or more areas of the foot and may include other types of sensors, including electrically conductive electrodes, vital sign monitoring sensors, accelerometers, gyroscopes, electromyography sensors, moisture sensors, and the like. Pressure sensors may be located in the plantar area of the foot (e.g., plantar forefoot, heel, midfoot, arch, etc.) to monitor pressure changes (and derived data, such as step count, impact forces, time on the ground, landing technique, and the like) during walking, jogging or running. Sensors may also be located in different regions of the foot, including, for example, central and lateral dorsal toe and/or forefoot locations, heel regions, ankle regions, and additional dorsal and/or lateral regions of the foot, depending on alternative applications and related embodiments.

In some embodiments, as described above, the SAS docking device may be configured for use with uninstrumented footwear, and provide a "dumb" docking device for detachably mating with a DED having sensing, data processing and/or storage and communications capabilities. In some embodiments, the SAS docking device may itself serve as the sensing assembly, and may carry one or more sensors and associated terminals.

Figure 12:
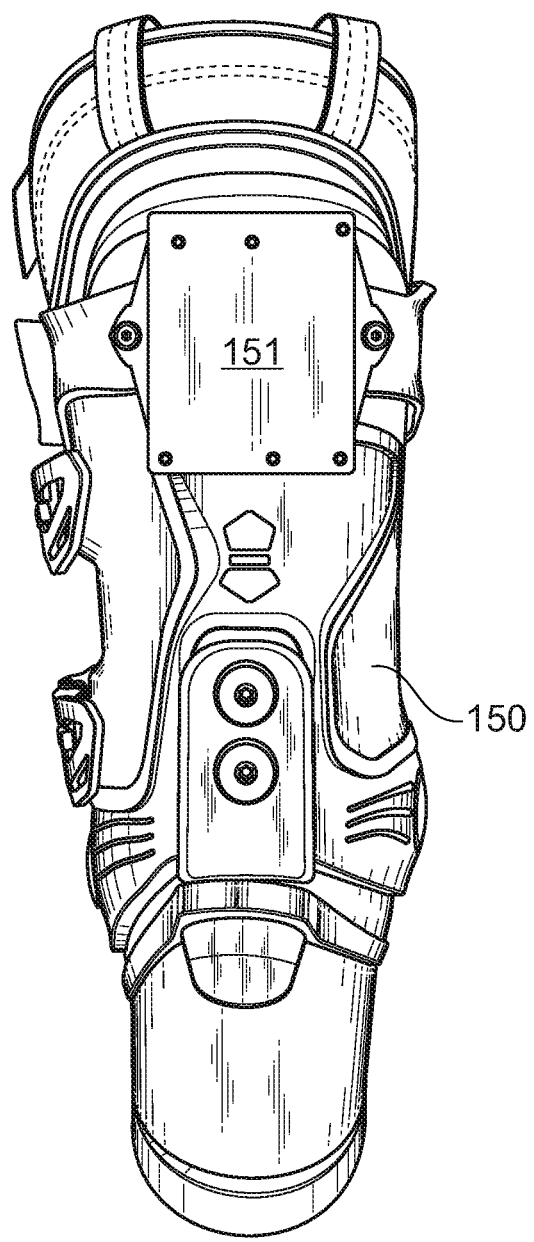
FIG. 12 illustrates an SAS/DED combination mounted on a ski boot and operatively coupled to sensors provided in the ski boot.

FIG. 12 illustrates an embodiment of an SAS and DED enclosure 151 attached to a ski boot 150. In this exemplary embodiment, the SAS/DED housing 151 is mounted or mountable to the back of ski boot 150 and comprises a single housing combining SAS and DED functions as described herein. Sensors communicating with the combined SAS/DED and associated with the ski boot may be located within the outer boot shell, for example, in the boot padding, insole, tongue, liner, or the like, and may be connected to the SAS/DED electronic device via various types of conductive pathways, such as traditional wiring, e-textile conductive traces, conductive yarns, threads or fibers, conductive inks/glues and the like. In this exemplary embodiment, sensors may comprise e-textile or traditional pressure sensors capable of detecting levels of pressure (and/or force and/or shear or derivative measurements) at one or more areas of the foot contact with the ski boot and may include other types of sensors, including electrically conductive electrodes, vital sign monitoring sensors, accelerometers, gyroscopes, electromyography sensors, moisture sensors, and the like. Pressure sensors may be located in the plantar area of the foot (e.g., plantar forefoot, heel, midfoot, arch, etc.) to monitor pressure changes (and derived data, impact forces, time on the ground, landing technique, and the like) during skiing activities.

Figure 13A:
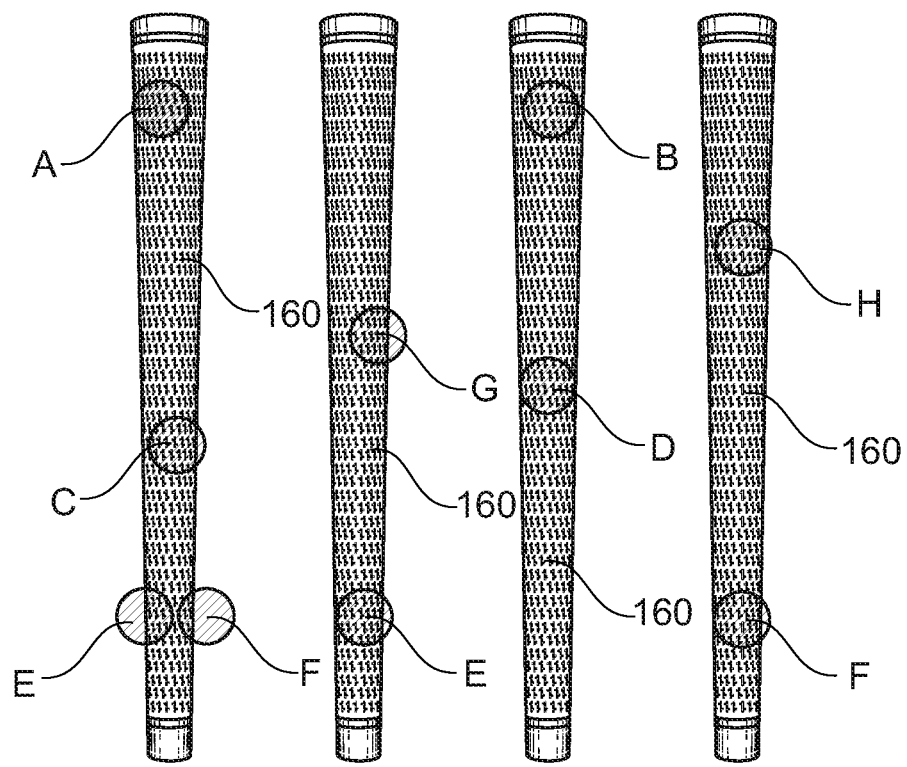
FIG. 13A schematically illustrates, from left to right, a first side view, front view, second side view and rear view showing the position of sensors positioned on a golf club grip, for example, underneath a grip wrap, and FIG. 13B schematically illustrates a golf grip having an SAS mounted on the end of the grip (on the left) and having a DED operably mounted to the SAS at the end of the grip (on the right).
Figure 13B:
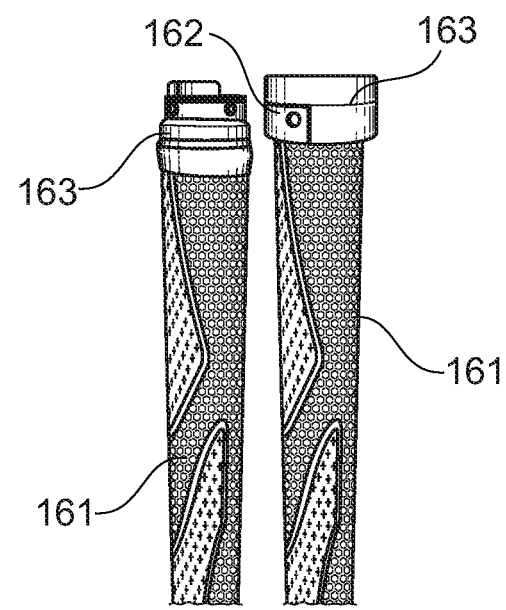

FIG. 13A illustrates exemplary locations of multiple sensors associated with a golf grip and shows, from left to right, a first side view, front view, second side view and rear view showing the position of sensors A-H positioned on a golf club grip, for example, underneath a grip wrap. The sensors may comprise pressure sensors such as e-textile or traditional pressure sensors capable of detecting levels of pressure (and/or force and/or shear or derivative measurements) exerted at one or more areas of the grip, for example, by the hand, during a swing. The golf grip (or other areas of the golf club) and may include other types of sensors, including electrically conductive electrodes, vital sign monitoring sensors, accelerometers, gyroscopes, electromyography sensors, moisture sensors, and the like. FIG. 13B illustrates wrapped golf grips 161 having the sensors of FIG. 13A positioned underneath the wrap, and having a conductive and common trace (positioned underneath the wrap) contacting each of the sensors and terminating at a distal end of the club. The sensor terminals contact mating terminals of an SAS docking device 162 sized and configured for securely mounting on distal end of the golf club, as shown on the left-hand diagram of FIG. 13B. The right-hand diagram of FIG. 13B shows the wrapped golf club grip 161 having an associated SAS docking device 162 and a DED core device 163 detachably mounted to the SAS docking device. In these embodiments, the DED core is mounted on the distal end of the golf grip, and connected to the SAS terminals via pogo-pin connections. A connector bus may be provided to drive signals from the sensors to the SAS docking device. Similar or complementary data may be acquired by providing sensors and related conductive traces, terminals, SAS and DED devices in association with a golf glove.

Electrical and electronic components embodied in an SAS and/or DED component are generally known. The components of each sensor channel may be divided in low-pass filters, high-pass filters, amplification elements, and other types of analog and digital elements. Each channel may be configured independently with different types of parameters. In this exemplary embodiment, each channel contains several electronic components such as resistors, capacitors and amplifiers. The values of these components can allow at least 10 different circuit configurations where the tow-pass, high-pass and amplification gain can be customized for different applications.

While sensor systems and accessories are described herein with respect to specific applications, it will be appreciated that such sensor systems and accessories may be implemented in footwear, including sports shoes (e.g., soccer shoes, basketball shoes, volleyball shoes, baseball shoes, tennis shoes, biking shoes and other types of sports shoes, as well as boots such as ski boots, hiking boots, and the like), in garments of various types, and in association with objects. Sensor-enabled as described, may also be used in conjunction with other sensor-enabled garments or accessories, such as heart-rate monitors, respiration monitors, heart-rate variability monitors, sensors measuring VO2max, torso acceleration, sweat volume and/or content, and the like, to provide even more comprehensive individual data.

While the present invention has been described above with reference to the accompanying drawings in which specific embodiments are shown and explained, it is to be understood that persons skilled in the art may modify the embodiments described herein without departing from the spirit and broad scope of the invention. Accordingly, the descriptions provided above are considered as being illustrative and exemplary of specific structures, aspects and features within the broad scope of the present invention and not as limiting the scope of the invention. The various embodiments described herein may be combined to provide further embodiments. The described devices, systems and methods may omit some elements or acts, may add other elements or acts, or may combine the elements or execute the acts in a different order than that illustrated, to achieve various advantages of the disclosure. These and other changes may be made to the disclosure in light of the above detailed description.

In the present description, where used, the term "about" means±20% of the indicated range, value, or structure, unless otherwise indicated. The terms "a" and "an" as used herein refer to "one or more" of the enumerated components. The use of the alternative (e.g., "or") should be understood to mean either one, both, or any combination thereof of the alternatives, unless otherwise expressly indicated. As used herein, the terms "include," "have" and "comprise" are used synonymously, and those terms, and variants thereof, are intended to be construed as non-limiting. The term "contact" and its derivatives should be understood to encompass both direct and indirect contact—i.e., contact includes direct, surface-on-surface contact, as well as indirect contact wherein one or more intermediate surfaces or components or materials is positioned between contacting surfaces or objects. It will be understood that when elements or components are described as being associated with one another, that association may be direct or indirect, and that association may include, without limitation, contact, mounting, bonding, adhering, incorporation and integration. In general, in the following claims, the terms used should not be construed to limit the disclosure to the specific embodiments disclosed in the specification.

We claim:

1. A sensor assembly comprising:
   at least one sensor in electrical communication with at least one electrically conductive trace that terminates at or in proximity to a signal transfer terminal, wherein the at least one sensor and at least one electrically conductive trace are sandwiched between two non-electrically conductive carrier layers;

a sensor acquisition system (SAS) having a plurality of contacts electrically coupled to an exposed electrically conductive trace termination positioned on a substrate;

a dedicated electronic device (DED) detachably mountable in the SAS component and having signal receipt terminals mate-able with contacts provided in the SAS component, and wherein at least one of the non-electrically conductive carrier layers is associated with a substrate having conductive trace terminations exposed on the substrate, wherein the substrate is selected from footwear, a footwear accessory, a garment, shorts, a shirt, a jersey, pants, a leotard, a belt, a strap, a glove, an object, sporting equipment, a shin guard, protective gear, a helmet, a ball, a bat, a stick, a striking implement, a racket, a golf club, a grip, a gaming implement, a gaming controller, a pillow, a sheet, a blanket, a cushion, an upholstered object, a cover, a seat cover, and a steering wheel cover.

2. The sensor assembly of claim 1, wherein the non-electrically conductive carrier layers comprise a polyvinyl chloride material.

3. The sensor assembly of claim 1, wherein the at least one sensor is a resistive pressure sensor comprising a material selected from the group consisting of: an e-textile material, a printable ink, a printable silicone, a thermoplastic elastomer, and combinations thereof.

4. The sensor assembly of claim 1, wherein the at least one electrically conductive trace comprises a material selected from the group consisting of: thread, yarn, textiles, fibers, a printable ink, a printable silicone, a thermoplastic elastomer, and combinations thereof.

5. The sensor assembly of claim 1, additionally comprising at least one signal transfer terminal in electrical communication with the at least one conductive trace.

6. The sensor assembly of claim 1, comprising at least one electrically conductive signal transfer trace and at least one common trace in electrical communication with each sensor.

7. The sensor assembly of claim 1, associated with a mask comprising a material selected from the group consisting of: paper, plastic, a film material, a sheet material, and combinations thereof.

8. The sensor assembly of claim 1, wherein the DED is configured to communicate with other DEDs within a communication range through a mesh network.

9. The sensor assembly of claim 1, wherein the SAS comprises a docking receptacle configured for securely receiving and electrically interfacing with a DED core device, wherein the SAS docking receptacle is configured for association with a substrate selected from the group consisting of: footwear, a footwear accessory, a garment, shorts, a shirt, a jersey, pants, a leotard, a belt, a strap, a glove, an object, sporting equipment, a shin guard, protective gear, a helmet, a ball, a bat, a stick, a striking implement, a racket, a golf club, a grip, a gaming implement, a gaming controller, a pillow, a sheet, a blanket, a cushion, an upholstered object, a cover, a seat cover, and a steering wheel cover; and wherein the SAS docking receptacle comprises a sealed housing having a dedicated electronic device (DED) core receiving cavity with a plurality of contacts for mating with complementary contacts on a mating DED core device.

10. The sensor acquisition system of claim 9, wherein the SAS docking receptacle has at least one recessed side wall.

11. The sensor assembly of claim 9, wherein the SAS docking receptacle has at least one internal alignment cavity sized and configured for mating with a complementary alignment boss provided on a mating DED core device.

12. The sensor assembly of claim 9, wherein the SAS docking receptacle additionally comprises a plurality of exposed conductive terminals and at least one common or ground conductive terminal configured for electrically interfacing with a sensor assembly associated with a substrate.

13. The sensor assembly of claim 9, wherein the SAS docking receptacle additionally comprises a component selected from the group consisting of: a sensor for sensing a physiological condition, a sensor for sensing an environmental condition, a sensor for sensing a location, an accelerometer, a gyroscope, a magnetometer, a 6-axis and/or 9-axis inertial measurement unit IMU; electronic components configured for data processing, data storage, data communication, an energy source, and antenna/e for wireless communications.

14. The sensor assembly of claim 9, wherein the DED core housing additionally comprises a component selected from the group consisting of: a sensor for sensing a physiological condition, a sensor for sensing an environmental condition, a sensor for sensing a location, an accelerometer; a gyroscope; a magnetometer; a 6-axis and/or 9-axis inertial measurement unit IMU; electronic components configured for data processing, data storage, data communication, an energy source, and antennae for wireless communications.

15. The sensor assembly of claim 9, wherein the DED core housing additionally comprises an enlarged exterior rim configured for conveniently detaching the DED core device from a corresponding SAS docking receptacle.

* * * * *